United States Patent
Lambers et al.

(10) Patent No.: US 11,785,976 B2
(45) Date of Patent: Oct. 17, 2023

(54) PROTEIN HYDROLYSATES AND METHODS OF MAKING SAME

(71) Applicant: MEAD JOHNSON NUTRITION COMPANY, Evansville, IN (US)

(72) Inventors: Teartse Tim Lambers, Nijmegen (NL); Cindy van Bommel, Zaltbommel (NL); Zihua Ao, Newburgh, IN (US); Anja Wittke, Boston, MA (US); Kelly Alina Dingess, Nijmegen (NL); Kasper Hettinga, Wageningen (NL)

(73) Assignee: Mead Johnson Nutrition Company, Evansville, IN (US)

( * ) Notice: Subject to any disclaimer, the term of this patent is extended or adjusted under 35 U.S.C. 154(b) by 199 days.

(21) Appl. No.: 17/233,716

(22) Filed: Apr. 19, 2021

(65) Prior Publication Data

US 2021/0235740 A1    Aug. 5, 2021

Related U.S. Application Data

(63) Continuation of application No. 15/376,432, filed on Dec. 12, 2016, now Pat. No. 10,980,269.

(51) Int. Cl.
| | | |
|---|---|---|
| A23L 33/18 | (2016.01) | |
| A23L 33/00 | (2016.01) | |
| A23L 33/19 | (2016.01) | |
| A23J 3/34 | (2006.01) | |
| A61K 38/01 | (2006.01) | |

(52) U.S. Cl.
CPC .............. *A23L 33/40* (2016.08); *A23J 3/344* (2013.01); *A23L 33/18* (2016.08); *A23L 33/19* (2016.08); *A61K 38/018* (2013.01); *A23Y 2220/73* (2013.01)

(58) Field of Classification Search
CPC .......... A23L 33/40; A23L 33/18; A23L 33/19; A23Y 2220/73
USPC .......................................................... 426/43
See application file for complete search history.

(56) References Cited

U.S. PATENT DOCUMENTS

| | | | |
|---|---|---|---|
| 4,791,193 A | 12/1988 | Okonogi et al. | |
| 5,169,666 A * | 12/1992 | Woychik | A23C 9/20 426/580 |
| 5,374,657 A | 12/1994 | Kyle | |
| 5,397,591 A | 3/1995 | Kyle | |
| 5,405,756 A | 4/1995 | Naito et al. | |
| 5,550,156 A | 8/1996 | Kyle | |
| 5,834,427 A | 11/1998 | Han et al. | |
| 5,846,939 A | 12/1998 | Miclo et al. | |
| 5,849,885 A | 12/1998 | Nuyens | |
| 5,881,491 A | 1/1999 | Nuijens | |
| 5,919,913 A | 7/1999 | Nuyens | |
| 6,005,791 A | 12/1999 | Gudesen et al. | |
| 6,045,854 A * | 4/2000 | Prieto | A23L 29/30 426/74 |
| 6,620,326 B1 | 9/2003 | Lihme | |
| 6,977,046 B2 | 12/2005 | Hubbuch | |
| 7,368,141 B2 | 5/2008 | Lihme | |
| 7,812,138 B2 | 10/2010 | Lihme | |
| 9,486,004 B2 | 11/2016 | Affolter et al. | |
| 10,639,334 B2 | 5/2020 | Banavara et al. | |
| 2004/0052860 A1* | 3/2004 | Reid | A61P 19/10 514/16.7 |
| 2004/0234666 A1 | 11/2004 | Law et al. | |
| 2006/0233752 A1* | 10/2006 | McMahon | A23L 33/135 424/93.1 |
| 2007/0104847 A1 | 5/2007 | O'Mahony et al. | |
| 2011/0217402 A1 | 9/2011 | van Tol et al. | |
| 2011/0293784 A1* | 12/2011 | Wittke | A61K 47/26 426/588 |
| 2013/0251829 A1 | 9/2013 | van Tol et al. | |
| 2015/0305385 A1 | 10/2015 | Chichlowski et al. | |
| 2021/0169177 A1 | 6/2021 | Sorensen et al. | |

FOREIGN PATENT DOCUMENTS

| | | |
|---|---|---|
| CN | 1852665 | 10/2006 |
| CN | 103153325 A | 6/2013 |
| CN | 105873457 A | 8/2016 |
| CN | 104073539 A | 3/2017 |
| EP | 0421309 A2 | 4/1991 |
| EP | 0631731 A1 | 1/1995 |
| EP | 2436389 A1 | 4/2012 |
| JP | H04173800 A | 6/1992 |
| JP | 2980362 B2 | 11/1999 |
| JP | 2006010357 | 1/2006 |
| NZ | 619383 | 11/2015 |

(Continued)

OTHER PUBLICATIONS

Gomez-Ruis et al. Eur. Food Res. Technol. 227: 1061-1067 (Year: 2008).*
Antal et al. Anal. Biochem. 288: 156-167 (Year: 2001).*
Caessens, et al. J. agric Food Chem. 45: 2935-2941 (Year: 1997).*
Indonesia First Office Action dated Apr. 26, 2021 issued in corresponding Indonesian Patent Application No. PID201904795.
Dallas, D., et al., "Endogenous human milk peptide release is greater after preterm birth than term birth," J. Nutr. Mar. 2015;145(3):425-33.
Dallas, D., et al., "Extensive in vivo human milk peptidomics reveals specific proteolysis yielding protective antimicrobial peptides," J. Proteome Res. May 3, 2013;12(5):2295-304.

(Continued)

*Primary Examiner* — Hamid R Badr
(74) *Attorney, Agent, or Firm* — Troutman Pepper Hamilton Sanders LLP; Ryan A. Schneider; Chris N. Davis (57) ABSTRACT

The present disclosure generally relates to methods of preparing protein hydrolysates for use in pediatric nutritional compositions. Specifically, alpha-, beta- and/or kappa casein enriched casein, acid casein or caseinates can be hydrolyzed with proteases such as trypsin (trypsin-like), chymotrypsin (chymotrypsin-like), pepsin and/or plasmin to produce a hydrolysate that is close to the peptide composition of human breast milk.

20 Claims, 1 Drawing Sheet
(1 of 1 Drawing Sheet(s) Filed in Color)

(56) References Cited

FOREIGN PATENT DOCUMENTS

| WO | 199200799 | 1/1992 |
|---|---|---|
| WO | 199218237 | 10/1992 |
| WO | 199717132 | 5/1997 |
| WO | 2003003847 | 1/2003 |
| WO | 2006124630 A2 | 11/2006 |
| WO | 2013142403 | 9/2013 |
| WO | 2014013060 A1 | 1/2014 |

OTHER PUBLICATIONS

Guererro, A., et al., "Mechanistic peptidomics: factors that dictate specificity in the formation of endogenous peptides in human milk," Mol Cell Proteomics Dec. 2014;12(12).

Wan, J., et al., "Peptidome analysis of human skim milk in term and preterm milk," Biochem Biophys Res Commun. Aug. 16, 2013;438(1):236-41.

Yadomae T., "Structure and biological activities of fungal beta-1,3-glucans," Yakugaku Zasshi. 2000;120:413-431.

Rival, S.G. el al. "Caseins and Casein Hydrolesates. 1. Lipoxgenase Inhibitory Properties", J. Agric. Food Chem. 49:287-294 (2001).

Poch, M. et al. "Bovine Milk K-Casein Trypsin Digest is a Growth Enhancer for the Genus *Bifidobacterium*" J. Agric. Food Chem. 39: 73-77 (1991).

Gomez-Ruiz, J, A. et al. "Antioxidant activity of ovine casein hydrolysates: Identification of active peptides by HPLC-MS/MS", Eur. Food Res. Technol. 227: 1061-1067 (2008).

Caessens, P.W.J.R. et al. "Plasmin Hydrolysis of β-Casein: Foaming and Emulsifying Properties of the Fractionated Hydrolysate", J. Agric. Food Chem. 45:2935-2941 (1997).

Fu Yanrong, et al., "Protein hydrolysis system of breast milk", pp. 56-59, Chinese Journal of Child Health Care, Dec. 7, 2016; Office Action.

Kleinman, R.E., "Pediatric Nutrition", Search Report.

* cited by examiner

PROTEIN HYDROLYSATES AND METHODS OF MAKING SAME

CROSS REFERENCE TO RELATED APPLICATIONS

This application is a Continuation of U.S. patent application Ser. No. 15/376,432 filed Dec. 12, 2016, which is incorporated by reference in its entirety.

TECHNICAL FIELD

The present disclosure relates to methods of preparing protein hydrolysates for use in pediatric nutritional compositions.

BACKGROUND

Exclusive breast feeding during the first six months after birth is recommended by the World Health Organization (WHO), and efforts are made to support and promote breast feeding amongst mothers worldwide. However, when a mother is unable to or chooses not to breast feed, it is necessary to provide an infant with a suitable substitute nutritional composition, such as an infant formula.

Accordingly, there is a need to provide nutritional compositions, such as infant formulas, that provide a pediatric subject with protein compositions close to those in human breast milk. The present disclosure addresses this need by providing methods for producing hydrolysate compositions that are more close to human breast milk than the protein sources available in presently available pediatric nutritional compositions.

BRIEF SUMMARY

Figure 1:
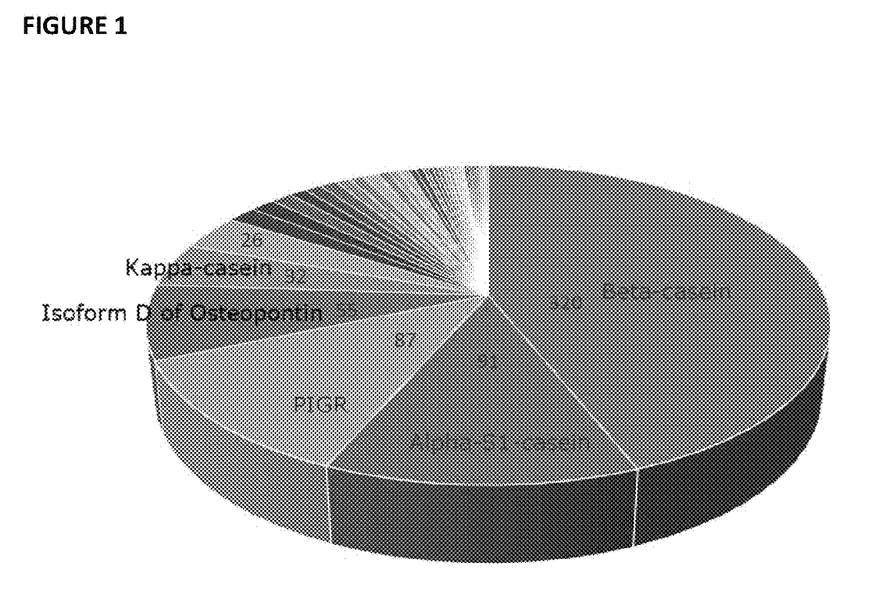
FIG. 1 shows a pie chart of human milk peptidome parent proteins. The endogenous peptidome of human milk (n=27) was determined by LC-MS/MS based peptidomics. The largest number of peptides originated from casein, in particular beta-casein.
Figure 2:
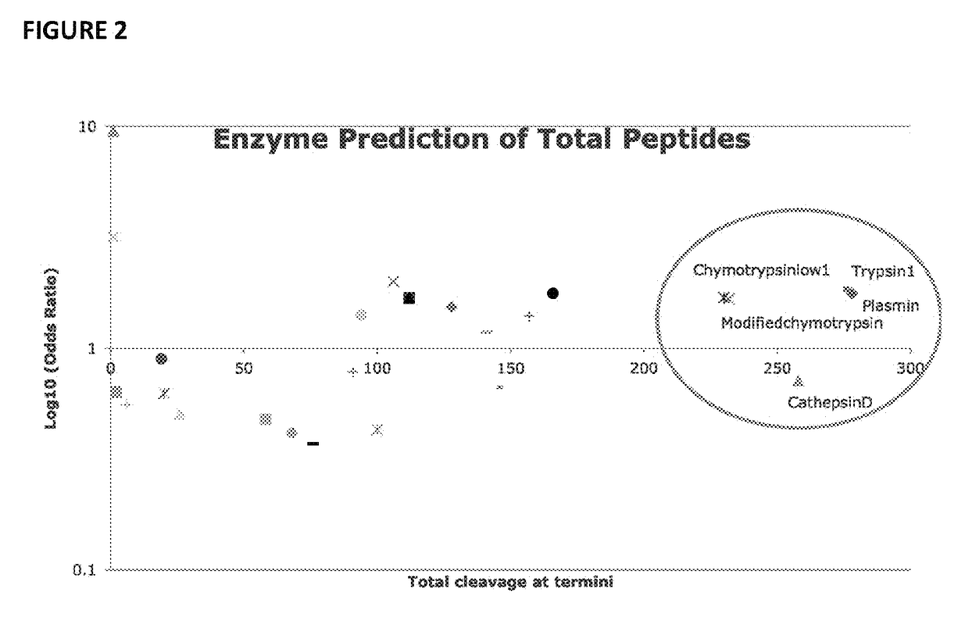
FIG. 2 shows an enzyme prediction of the total human milk peptidome. The endogenous peptidome of human milk (n=27) was determined by LC-MS/MS based peptidomics and using EnzymePredictor software proteases were predicted.

Applicants have determined the peptide composition of human breast milk (see, FIG. 1) and performed in silico analyses to predict which proteases produced the peptides present in human milk (see, FIG. 2). The analysis of the peptide composition (i.e., "peptidome") of human breast milk has led to the discovery of methods for hydrolyzing non-human (e.g., bovine) protein sources using proteases as described herein, to provide a peptide composition for use in a nutritional composition for pediatric subjects that are closer to human milk than prior art compositions. Thus, the present disclosure relates in part to the preparation of hydrolysates for use in pediatric nutritional compositions, e.g., an infant formula, wherein the hydrolysates are prepared so as to comprise a peptide composition close to that found in human milk.

In certain embodiments, the disclosure relates to a method for preparing a protein hydrolysate for use in a nutritional composition. The method can include hydrolyzing milk protein preparations such as a casein, acid casein or caseinate using serine proteases such as trypsin (or trypsin-like), chymotrypsin (or chymotrypsin-like) or plasmin, or any combination thereof or aspartyl proteases such as pepsin, or any combination thereof. Trypsin-like refers to proteolytic enzymes having proteolytic activity similar to that of trypsin, for example, proteolytic enzymes that cleave peptide bonds following a positively charged amino acid (e.g., lysine or arginine). Chymotrypsin-like refers to proteolytic enzymes having proteolytic activity similar to that of chymotrypsin, for example, proteolytic enzymes that cleave peptide bonds following a medium- to large-sized hydrophobic residue such as tyrosine, phenylalanine, and tryptophan.

In certain embodiments, trypsin, chymotrypsin and plasmin are used. In certain embodiments, trypsin and chymotrypsin are used. In certain embodiments, trypsin and plasmin are used. In certain embodiments, chymotrypsin and plasmin are used. In certain embodiments, trypsin, chymotrypsin, plasmin and pepsin are used. In certain embodiments, trypsin, chymotrypsin and pepsin are used. In certain embodiments, trypsin, plasmin and pepsin are used. In certain embodiments, chymotrypsin, plasmin and pepsin are used. The proteases can be derived from animal and/or microbial sources.

In certain embodiments, the milk protein preparation is a casein, acid casein or caseinate, such as a beta-casein enriched casein, acid casein or caseinate, an alpha-casein enriched casein, acid casein or caseinate, and/or a kappa-casein enriched casein, acid casein or caseinate. In certain embodiments, the casein, acid casein or caseinate is beta-casein enriched, and comprises between about 40-95% beta-casein. In certain embodiments, the casein, acid casein or caseinate is alpha-casein enriched, and comprises between about 50-95% alpha-casein. In certain embodiments, the alpha-casein enriched casein, acid casein or caseinate further comprises between about 15-95% kappa-casein. In certain embodiments, the casein, acid casein or caseinate is kappa-casein enriched and comprises between about 15-95% kappa-casein. In certain embodiments, the casein, acid casein or caseinate may contain whey proteins in an amount no greater than 20%.

In another aspect, the disclosure relates to a method for preparing a protein hydrolysate for use in a nutritional composition, the method comprising hydrolyzing polymeric immunoglobulin receptor (PIGR), osteopontin, bile-salt activated lipase and/or clusterin using a protease or proteases. In certain embodiments, the protease is trypsin, chymotrypsin, pepsin and/or plasmin.

In certain embodiments, the method also entails including the protein hydrolysate in a nutritional composition. The nutritional composition can be a pediatric nutritional composition such as an infant formula. The nutritional composition can include a protein source, a lipid source, and/or a carbohydrate source. The nutritional composition can also include a prebiotic and/or a probiotic. The probiotic can be a *Lactobacillus* species, such as *Lactobacillus rhamnosus* GG. The probiotic can be non-viable or viable. The probiotic can be present in an amount ranging from about $1 \times 10^5$ cfu/100 kcals to about $1.5 \times 10^9$ cfu/100 kcals.

In certain embodiments, the nutritional composition can include a human milk oligosaccharide (HMO), a long chain polyunsaturated fatty acid (e.g., docosahexaenoic acid and/or arachidonic acid), or a source of β-glucan (e.g., β-1,3-glucan).

In certain embodiments, the disclosure relates to a nutritional composition comprising a protein hydrolysate as described herein.

It is to be understood that both the foregoing general description and the following detailed description present embodiments of the disclosure and are intended to provide an overview or framework for understanding the nature and character of the disclosure as it is claimed. The description serves to explain the principles and operations of the claimed subject matter. Other and further features and advantages of the present disclosure will be readily apparent to those skilled in the art upon a reading of the following disclosure.

BRIEF DESCRIPTION OF THE FIGURES

The accompanying Figures, which are incorporated in and constitute a part of this specification, illustrate several aspects described below. [The patent or application file contains at least one drawing executed in color. Copies of this patent or patent application publication with color drawing(s) will be provided by the Office upon request and payment of the necessary fee.

DETAILED DESCRIPTION

Reference now will be made in detail to the embodiments of the present disclosure, one or more examples of which are set forth herein below. Each example is provided by way of explanation of the nutritional composition of the present disclosure and is not a limitation. In fact, it will be apparent to those skilled in the art that various modifications and variations can be made to the teachings of the present disclosure without departing from the scope or spirit of the disclosure. For instance, features illustrated or described as part of one embodiment, can be used with another embodiment to yield a still further embodiment.

Thus, it is intended that the present disclosure covers such modifications and variations as come within the scope of the appended claims and their equivalents. Other objects, features and aspects of the present disclosure are disclosed in or are obvious from the following detailed description. It is to be understood by one of ordinary skill in the art that the present discussion is a description of exemplary embodiments only and is not intended as limiting the broader aspects of the present disclosure.

"Nutritional composition" means a substance or formulation that satisfies at least a portion of a pediatric subject's nutrient requirements. The terms "nutritional(s)," "nutritional formula(s)," "enteral nutritional(s)," "nutritional composition(s)," and "nutritional supplement(s)" are used interchangeably throughout the present disclosure to refer to liquids, powders, gels, pastes, solids, concentrates, suspensions, or ready-to-use forms of enteral formulas, oral formulas, formulas for infants, formulas for pediatric subjects, formulas for children, growing-up milks and/or formulas for adults, such as women who are lactating or pregnant. In particular embodiments, the nutritional compositions are for pediatric subjects, including infants and children.

The term "enteral" means through or within the gastrointestinal, or digestive, tract. "Enteral administration" includes oral feeding, intragastric feeding, transpyloric administration, or any other administration into the digestive tract.

"Pediatric subject" includes both infants and children, and refers herein to a human that is less than thirteen years of age. In some embodiments, a pediatric subject refers to a human subject that is less than eight years old. In other embodiments, a pediatric subject refers to a human subject between about one and about six years of age or about one and about three years of age. In still further embodiments, a pediatric subject refers to a human subject between about 6 and about 12 years of age.

"Infant" means a subject having an age of not more than about one year and includes infants from about zero to about twelve months. The term infant includes low birth weight infants, very low birth weight infants, and preterm infants. "Preterm" means an infant born before the end of the 37th week of gestation, while "full term" means an infant born after the end of the 37th week of gestation.

"Child" means a subject ranging in age from about twelve months to about thirteen years. In some embodiments, a child is a subject between the ages of one and twelve years old. In other embodiments, the terms "children" or "child" refer to subjects that are between about one and about six years old, between about one and about three years old, or between about seven and about twelve years old. In other embodiments, the terms "children" or "child" refer to any range of ages between about 12 months and about 13 years.

"Children's nutritional product" refers to a composition that satisfies at least a portion of the nutrient requirements of a child. A growing-up milk is an example of a children's nutritional product.

"Infant formula" means a composition that satisfies at least a portion of the nutrient requirements of an infant. In the United States, the content of an infant formula is dictated by the federal regulations set forth at 21 C.F.R. Sections 100, 106, and 107. These regulations define macronutrient, vitamin, mineral, and other ingredient levels in an effort to simulate the nutritional and other properties of human breast milk.

The term "growing-up milk" refers to a broad category of nutritional compositions intended to be used as a part of a diverse diet in order to support the normal growth and development of a child between the ages of about 1 and about 6 years of age.

"Milk-based" means comprising at least one component that has been drawn or extracted from the mammary gland of a mammal. In some embodiments, a milk-based nutritional composition comprises components of milk that are derived from domesticated ungulates, ruminants or other mammals or any combination thereof. Moreover, in some embodiments, milk-based means comprising bovine casein, whey, lactose, or any combination thereof. Further, "milk-based nutritional composition" may refer to any composition comprising any milk-derived or milk-based product known in the art.

"Nutritionally complete" means a composition that may be used as the sole source of nutrition, which would supply essentially all of the required daily amounts of vitamins, minerals, and/or trace elements in combination with proteins, carbohydrates, and lipids. Indeed, "nutritionally complete" describes a nutritional composition that provides adequate amounts of carbohydrates, lipids, essential fatty acids, proteins, essential amino acids, conditionally essential amino acids, vitamins, minerals and energy required to support normal growth and development of a subject.

Therefore, a nutritional composition that is "nutritionally complete" for a preterm infant will, by definition, provide qualitatively and quantitatively adequate amounts of carbohydrates, lipids, essential fatty acids, proteins, essential amino acids, conditionally essential amino acids, vitamins, minerals, and energy required for growth of the preterm infant.

A nutritional composition that is "nutritionally complete" for a term infant will, by definition, provide qualitatively and quantitatively adequate amounts of all carbohydrates, lipids, essential fatty acids, proteins, essential amino acids, conditionally essential amino acids, vitamins, minerals, and energy required for growth of the term infant.

A nutritional composition that is "nutritionally complete" for a child will, by definition, provide qualitatively and quantitatively adequate amounts of all carbohydrates, lipids, essential fatty acids, proteins, essential amino acids, conditionally essential amino acids, vitamins, minerals, and energy required for growth of a child.

As applied to nutrients, the term "essential" refers to any nutrient that cannot be synthesized by the body in amounts sufficient for normal growth and to maintain health and that, therefore, must be supplied by the diet. The term "conditionally essential" as applied to nutrients means that the nutrient must be supplied by the diet under conditions when adequate amounts of the precursor compound is unavailable to the body for endogenous synthesis to occur.

"Nutritional supplement" or "supplement" refers to a formulation that contains a nutritionally relevant amount of at least one nutrient. For example, supplements described herein may provide at least one nutrient for a human subject, such as a lactating or pregnant female.

The term "protein equivalent" or "protein equivalent source" includes any protein source, such as soy, egg, whey, or casein, as well as non-protein sources, such as peptides or amino acids. Further, the protein equivalent source can be any used in the art, e.g., nonfat milk, whey protein, casein, soy protein, hydrolyzed protein, peptides, amino acids, and the like. Bovine milk protein sources useful in practicing the present disclosure include, but are not limited to, milk protein powders, milk protein concentrates, milk protein isolates, nonfat milk solids, nonfat milk, nonfat dry milk, whey protein, whey protein isolates, whey protein concentrates, sweet whey, acid whey, casein, acid casein, caseinate (e.g. sodium caseinate, sodium calcium caseinate, calcium caseinate), soy bean proteins, and any combinations thereof. The protein equivalent source can, in some embodiments comprise hydrolyzed protein, including partially hydrolyzed protein and extensively hydrolyzed protein. The protein equivalent source may, in some embodiments, include intact protein.

The term "protein equivalent source" also encompasses free amino acids. In some embodiments, the amino acids may comprise, but are not limited to, histidine, isoleucine, leucine, lysine, methionine, cysteine, phenylalanine, tyrosine, threonine, tryptophan, valine, alanine, arginine, asparagine, aspartic acid, glutamic acid, glutamine, glycine, proline, serine, carnitine, taurine and mixtures thereof. In some embodiments, the amino acids may be branched chain amino acids. In certain other embodiments, small amino acid peptides may be included as the protein component of the nutritional composition. Such small amino acid peptides may be naturally occurring or synthesized.

The term "essential amino acid" as used herein refers to an amino acid that cannot be synthesized de novo by the organism being considered or that is produced in an insufficient amount, and therefore must be supplied by diet. For example, in some embodiments, where the target subject is a human, an essential amino acid is one that cannot be synthesized de novo by a human.

The term "non-essential amino acid" as used herein refers to an amino acid that can be synthesized by the organism or derived by the organism from essential amino acids. For example, in some embodiments, where the target subject is a human, a non-essential amino acid is one that can be synthesized in the human body or derived in the human body from essential amino acids.

"Probiotic" means a microorganism with low or no pathogenicity that exerts at least one beneficial effect on the health of the host. An example of a probiotic is LGG.

In certain embodiments, the probiotic(s) may be viable or non-viable. As used herein, the term "viable", refers to live microorganisms. The term "non-viable" or "non-viable probiotic" means non-living probiotic microorganisms, their cellular components and/or metabolites thereof. Such non-viable probiotics may have been heat-killed or otherwise inactivated, but they retain the ability to favorably influence the health of the host. The probiotics useful in the present disclosure may be naturally-occurring, synthetic or developed through the genetic manipulation of organisms, whether such source is now known or later developed.

The term "non-viable probiotic" means a probiotic wherein the metabolic activity or reproductive ability of the referenced probiotic has been reduced or destroyed. More specifically, "non-viable" or "non-viable probiotic" means non-living probiotic microorganisms, their cellular components and/or metabolites thereof. Such non-viable probiotics may have been heat-killed or otherwise inactivated. The "non-viable probiotic" does, however, still retain, at the cellular level, its cell structure or other structure associated with the cell, for example exopolysaccharide and at least a portion its biological glycol-protein and DNA/RNA structure and thus retains the ability to favorably influence the health of the host. Contrariwise, the term "viable" refers to live microorganisms. As used herein, the term "non-viable" is synonymous with "inactivated".

The term "equivalent" or "cell equivalent" refers to the level of non-viable, non-replicating probiotics equivalent to an equal number of viable cells. The term "non-replicating" is to be understood as the amount of non-replicating microorganisms obtained from the same amount of replicating bacteria (cfu/g), including inactivated probiotics, fragments of DNA, cell wall or cytoplasmic compounds. In other words, the quantity of non-living, non-replicating organisms is expressed in terms of cfu as if all the microorganisms were alive, regardless whether they are dead, non-replicating, inactivated, fragmented etc.

"Prebiotic" means a non-digestible food ingredient that beneficially affects the host by selectively stimulating the growth and/or activity of one or a limited number of beneficial gut bacteria in the digestive tract, selective reduction in gut pathogens, or favorable influence on gut short chain fatty acid profile that can improve the health of the host.

"β-glucan" means all β-glucan, including both β-1,3-glucan and β-1,3;1,6-glucan, as each is a specific type of β-glucan. Moreover, β-1,3;1,6-glucan is a type of β-1,3-glucan. Therefore, the term "β-1,3-glucan" includes β-1,3;1,6-glucan.

All percentages, parts and ratios as used herein are by weight of the total formulation, unless otherwise specified.

The nutritional composition of the present disclosure may be free or substantially free of any optional or selected ingredients described herein. In this context, and unless otherwise specified, the term "substantially free" means that the selected composition may contain less than a functional amount of the optional ingredient, typically less than 0.1% by weight, and also, including zero percent by weight of such optional or selected ingredient. The compositions described herein may be free or substantially free of any one or more of the following components: protein, lipid, GOS, PDX, prebiotics, LGG, probiotics, DHA, ARA, LCPUFAs, beta glucan (or any specific beta glucan described herein), etc.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The compositions and methods of the present disclosure, including components thereof, can comprise, consist of, or consist essentially of the essential elements and limitations of the embodiments described herein, as well as any additional or optional ingredients, components or limitations described herein or otherwise useful in nutritional compositions.

As used herein, the term "about" should be construed to refer to both of the numbers specified in any range. Any reference to a range should be considered as providing support for any subset within that range.

Methods

The methods herein relate to the analysis of the peptide composition (i.e., "peptidome") of human breast milk and discovery of methods for providing a peptide composition for use in a nutritional composition for pediatric subjects that more closely mimics human milk. Thus, the present disclosure relates in part to the preparation of hydrolysates for use in pediatric nutritional compositions, e.g., an infant formula, wherein the hydrolysates are prepared so as to comprise a protein and peptide-containing composition close to that found in human milk.

The methods disclosed herein relate, in part, to preparing hydrolysates of beta-, alpha- or kappa-enriched casein, acid casein or caseinates, for use in, e.g., nutritional formulations. Casein refers to a family of related phosphoproteins, including beta-casein, alpha-casein and kappa-casein. Bovine casein is commercially available from a variety of sources. In certain embodiments, a casein that is enriched in beta-, alpha- or kappa-casein is used. Methods for enriching beta-casein (see, e.g., U.S. Patent Publication No. 20070104847) and alpha- and kappa-casein (see, e.g., WO2003003847) are known in the art. An acid casein or a caseinate (e.g. sodium caseinate, sodium calcium caseinate, calcium caseinate) enriched in beta-, alpha-, or kappa-casein can also be used. Caseinates are typically formed by a reaction of acid casein protein with an alkali.

The methods disclosed herein further relate to preparing hydrolysates of polymeric immunoglobulin receptor (PIGR), osteopontin, bile-salt activated lipase and/or clusterin with any one or more of the proteases described herein.

As described herein, hydrolysates can be made using one or more proteases. Suitable proteases include trypsin, chymotrypsin, plasmin, pepsin, or any combination thereof. In certain embodiments, trypsin, chymotrypsin and plasmin are used. In certain embodiments, trypsin and chymotrypsin are used. In certain embodiments, trypsin and plasmin are used. In certain embodiments, chymotrypsin and plasmin are used. In certain embodiments, trypsin, chymotrypsin, plasmin and pepsin are used. In certain embodiments, trypsin, chymotrypsin and pepsin are used. In certain embodiments, trypsin, plasmin and pepsin are used. In certain embodiments, chymotrypsin, plasmin and pepsin are used. In certain embodiments, cathepsin D is also used (e.g., trypsin, chymotrypsin, plasmin, and cathepsin D are used; trypsin, chymotrypsin, and cathepsin D are used; trypsin, plasmin, and cathepsin D are used; chymotrypsin, plasmin, and cathepsin D are used; trypsin, chymotrypsin, plasmin, pepsin and cathepsin D are used; trypsin, chymotrypsin, pepsin and cathepsin D are used; trypsin, plasmin, pepsin and cathepsin D are used, chymotrypsin, plasmin, pepsin and cathepsin D are used). In certain embodiments, exonucleases are used. Proteases are known in the art and can be obtained from any number of manufacturers, including, for example, from Sigma Aldrich, St. Louis, Mo. and Worthington Biochemical Corporation, Lakewood, N.J.

Methods for preparing casein hydrolysates are known in the art and are described, for example, in Japanese Patent Application No. JP2006010357 and in New Zealand Patent Application No. NZ619383, the disclosures of which are hereby incorporated by reference for all purposes.

In certain embodiments, to prepare a hydrolysate, the protein (e.g., a beta-casein enriched casein) is dissolved or dispersed in a solvent such as water (e.g., distilled water), which may include an acid or alkaline or their salts. The concentration of the solution can be between about 1% and about 75% by weight, about 1% and about 50% by weight, about 1% and about 40% by weight, about 1% and about 30% by weight, about 1% and about 20% by weight, about 1% and about 15% by weight, about 1 and about 10% by weight, about 5% and about 15% by weight, about 5% and about 10% by weight.

The pH of the solution is then adjusted to within the operable range for the protease or proteases to be used. Substrate concentration, enzyme concentration, reaction temperature, reaction time, etc., are determined for the particular protease used. Reaction conditions for a given enzyme are known in the art and are typically provided by the manufacturer of the enzyme. For example, the pH range can be adjusted between pH 1 and pH 10, preferably in a range of 2-9. For some enzymes, pH is preferably in a range of 6-9; whereas, pH for other enzymes is preferably in a range of 2-4. The pH can be adjusted during the process of enzyme digestion.

Progression of the reaction can be monitored by, for example, collecting a sample of the reaction solution at various time intervals, and measuring the extent of protein degradation, and optionally measuring molecular weight distribution of the protein hydrolysates.

The reaction may be stopped by any means known in the art, for example, by addition of hydrochloride acid solution and/or heat inactivation treatment. Heat deactivation treatment conditions (heating temperature, heating time, etc.), can be determined based upon the thermal stability of the enzyme used. The treatment can also combined with other technologies such as filtration, microfiltration, ultrafiltration, or nanofiltration to reduce and deactivate the enzyme proteins.

After stopping the enzymatic reaction, the resulting hydrolysate may be purified using one or more of filtration, microfiltration, membrane separation processes such as ultrafiltration membrane, resin adsorption separation, from column chromatography. Membrane separation processes can be carried out using any apparatus known in the art. For example, microfiltration modules and ultrafiltration modules can be used to filter the hydrolysate, which is obtained as a membrane permeant fraction. Resin adsorption separation can be carried out in any manner known in the art, for example, using resins, ion exchange resins, chelate resins, affinity adsorbent resin, a synthetic adsorbent, and high performance liquid chromatography resin.

Properties of the peptide hydrolysate can be tested and evaluated by, e.g., mass spectrometry and/or standard nitrogen and degree of hydrolyses measurements. An exemplary mass spectrometer suitable for use with the methods described herein is a high-performance liquid chromatograph triple quadrupole mass spectrometer (LC/MS/MS, Waters TQD). Hydrolysate can be separated by gradient analysis using chromatography, e.g., a reverse phase ODS column as a separation column and a 0.1% formic acid aqueous solution and 0.1% formic acid containing acetonitrile as eluents prior to measurement by mass spectrometer. Specific peptide content can be determined using a calibration curve with a synthetic peptide as a standard and/or labeled peptide standards.

Nutritional Compositions

The protein hydrolysates prepared by the methods of the invention can be included in a nutritional composition, e.g., a pediatric nutritional composition, individually, or in combination. In certain embodiments, the protein hydrolysate is present in an amount of about 0.036 g/100 kcal to about 3 g/100 kcal of the nutritional composition, or about 0.042 g/100 Kcal to about 2.5 g/100 Kcal, about 0.042 g/100 Kcal to 1.5 g/100 Kcal, about 0.042 g/100 Kcal to about 1 g/100 Kcal, or about 0.042 g/100 Kcal to about 0.5 g/100 Kcal. In certain embodiments, the hydrolysate is included in a nutritional composition as the sole source of protein. Additional components that can be added to the nutritional composition are described below.

In certain embodiments, beta-casein peptides provide about 25% to about 60% (e.g., about 30% to about 50%, about 35% to about 45%) of the total peptides in the nutritional composition. In certain embodiments, alpha-casein peptides provide about 5% to about 25% (e.g., about 10% to about 20%, about 12% to about 18%) of the total peptides in the nutritional composition. In certain embodiments, PIGR peptides provide about 5% to about 25% (e.g., about 10% to about 20%, about 12% to about 18%) of the total peptides in the nutritional composition. In certain embodiments, osteopontin peptides provide about 1% to about 15% (e.g., about 5% to about 10%, about 6% to about 8%) of the total peptides in the nutritional composition. In certain embodiments, kappa-casein peptides provide about 1% to about 10% (e.g., about 2% to about 8%, about 3% to about 5%) of the total peptides in the nutritional composition. In certain embodiments, bile salt-activated lipase peptides provide about 1% to about 10% (e.g., about 2% to about 8%, about 3% to about 5%) of the total peptides in the nutritional composition. In certain embodiments, clusterin peptides provide about 0.5% to about 5% (e.g., about 1% to about 3%, about 2%) of the total peptides in the nutritional composition.

The nutritional compositions described herein can also include a human milk oligosaccharide (HMO). The term "HMOs" or "human milk oligosaccharides" refers generally to a number of complex carbohydrates found in human breast milk that can be in either acidic or neutral form. In certain embodiments, the HMO is 2'-fucosyllactose (2FL), 3'-fucosyllactose (3FL), 3'sialyllactose (3SL), 6'sialyllactose (6SL), lacto-N-biose (LNB), lacto-N-neotetraose (LnNT), lacto-N-tetraose (LNT), lacto-N-fucopentaose, lacto-N-fucopentaose I, lacto-N-fucopentaose II, lacto-N-fucopentaose III, lacto-N-fucopentaose V, lacto-N-neofucopentaose, lactodifucotetraose, lacto-N-difucohexaose II, lacto-N-neodifucohexaose II, para-lacto-N-neohexaose, 3' sialyl-3fucosyl-lactose, sialy-lacto-N-tetraose, or any combination thereof. 3'sialyllactose, 6'sialyllactose contribute sialic acid, which is an important nutrient for brain development and cognitive function. Precursors of HMOs, such as sialic acid, fucose, N-acetylglucosamine, or a combination thereof, also may be included in the present compositions.

HMOs may be isolated or enriched from milk or produced via microbial fermentation, enzymatic processes, chemical synthesis, or a combination thereof. For example, the HMOs disclosed herein may be derived from cow milk, cow colostrum, goat milk, goat colostrum, horse milk, horse colostrum, or any combination thereof.

HMOs are believed to correlate with the presence of beneficial infant specific *Bifidobacterium* species, such as *B. longum*, *B. infantis*, *B. breve*, and *B. bifidium* in breast fed infants. Accordingly, the compositions and methods described herein can be useful in increasing or maintaining the amount of one or more of *B. longum*, *B. infantis*, *B. breve*, and *B. bifidium* in the gastrointestinal tract (e.g., gut) of the pediatric subject. In certain embodiments, providing to a pediatric subject HMOs similar to those in the mother's breast milk can affect the composition of gastrointestinal bacteria in the pediatric subject, and make the composition of gastrointestinal bacteria more similar to that which would occur if the pediatric subject consumed his mother's breast milk.

The HMOs, in certain embodiments, is present in the compositions in an amount ranging from about 0.005 g/100 kcal to about 1 g/100 kcal. In other embodiments, the HMOs may be present in an amount ranging from about 0.01 g/100 kcal to about 1 g/100 kcal, about 0.02 g/100 kcal to about 1 g/100 kcal, about 0.3 g to about 1 g/100 kcal, about 0.1 g/100 kcal to about 0.8 g/100 kcal, or about 0.1 g/100 kcal to about 0.5 g/100 kcal.

In some embodiments the nutritional compositions include from about 0.01 g/100 kcal to about 0.8 g/100 kcal of sialylated HMOs. In other embodiments, the nutritional compositions include from about 0.03 g/100 kcal to about 0.6 g/100 kcal of sialylated HMOs. Still in some embodiments, then nutritional compositions include from about 0.04 g/100 kcal to about 0.8 g/100 kcal of sialylated HMOs. Still in other embodiments, the nutritional compositions include from about 0.05 g/100 kcal to about 0.6 g/100 kcal of sialylated HMOs.

In some embodiments, the nutritional compositions include from about 0.01 g/100 kcal to about 0.2 g/100 kcal of fucosylated HMOs. In some embodiments, the nutritional compositions include from about 0.02 g/100 kcal to about 0.2 g/100 kcal of fucosylated HMOs. In some embodiments, the nutritional compositions include from about 0.05 g/100 kcal to about 0.1 g/100 kcal of fucosylated HMOs.

In some embodiments, the nutritional compositions include from about 0.01 g/100 kcal to about 0.5 g/100 kcal of HMOs that are neither sialyated nor fucosylated. In certain embodiments, the nutritional compositions include from about 0.025 g/100 kcal to about 0.5 g/100 kcal of HMOs that are neither sialylated nor fucosylated. In other embodiments, the nutritional compositions contain from about 0.25 g/100 kcal to about 0.7 g/100 kcal of HMOs that are neither sialylated nor fucosylated. Indeed, in certain embodiments, the majority of the HMOs included in the nutritional compositions are neither sialylated nor fucosylated.

In some embodiments, the nutritional composition may be formulated to include a certain weight percentage of HMOs based on the total amount of carbohydrates present in the nutritional compositions. Accordingly, in some embodiments the nutritional composition may include from about 0.1 wt % to about 25 wt % HMOs based on the total weight of carbohydrates in the nutritional composition. In some embodiments, the nutritional composition includes from about 0.5 wt % to about 25 wt % HMOs based on the total weight of carbohydrates in the nutritional composition. In some embodiments, the nutritional composition includes from about 1 wt % to about 25 wt % HMOs based on the total weight of carbohydrates in the nutritional composition. In some embodiments, the nutritional composition includes from about 2 wt % to about 20 wt % HMOs based on the total weight of the carbohydrates in the nutritional composition. Still in some embodiments, the nutritional composition includes from about 5 wt % to about 15 wt % HMOs based on the total weight of the carbohydrates in the nutritional composition. In some embodiments, the nutritional composition includes from about 8 wt % to about 12 wt % HMOs based on the total weight of the carbohydrates in the nutritional composition. Still, in certain embodiments, the nutritional composition is formulated to include from about 0.1 wt % to about 5 wt % of HMOs based on the total weight of the carbohydrates in the nutritional composition.

Precursors of HMOs, such as sialic acid, fucose, N-acetyl-glucosamine, or a combination thereof, also may be included in the present compositions.

The nutritional composition may also contain one or more prebiotics (also referred to as a prebiotic source), in addition to HMOs, in certain embodiments. Prebiotics can stimulate the growth and/or activity of ingested probiotic microorganisms, selectively reduce pathogens found in the gut, and favorably influence the short chain fatty acid profile of the gut. Such prebiotics may be naturally-occurring, synthetic, or developed through the genetic manipulation of organisms and/or plants, whether such new source is now known or developed later. Prebiotics useful in the present disclosure may include oligosaccharides, polysaccharides, and other prebiotics that contain fructose, xylose, soya, galactose, glucose and mannose.

More specifically, prebiotics useful in the present disclosure may include polydextrose, polydextrose powder, lactulose, lactosucrose, raffinose, gluco-oligosaccharide, inulin, fructo-oligosaccharide, isomalto-oligosaccharide, soybean oligosaccharides, lactosucrose, xylo-oligosaccharide, chito-oligosaccharide, manno-oligosaccharide, aribino-oligosaccharide, sialyl-oligosaccharide, fuco-oligosaccharide, galacto-oligosaccharide, and gentio-oligosaccharides. In some embodiments, the total amount of prebiotics present in the nutritional composition may be from about 0.1 g/100 kcal to about 1.5 g/100 kcal. In certain embodiments, the total amount of prebiotics present in the nutritional composition may be from about 0.3 g/100 kcal to about 1.0 g/100 kcal. Moreover, the nutritional composition may comprise a prebiotic component comprising polydextrose ("PDX") and/or galacto-oligosaccharide ("GOS"). In some embodiments, the prebiotic component comprises at least 20% GOS, PDX or a mixture thereof.

In certain embodiments, the HMO component may be included in combination with GOS and PDX. The nutritional composition can comprise from about 0.1 g/100 kcal to about 5 g/100 kcal of prebiotics, including GOS, PDX, and HMOs. Still in certain embodiments, the nutritional composition can include from about 0.1 g/100 kcal to about 4 g/100 kcal of prebiotics, including GOS, PDX, and HMOs.

In certain embodiments, the prebiotic component comprises both GOS and PDX. The GOS and PDX may be present in a ratio of about 1:9 to about 9:1 by weight. In other embodiments, the GOS and PDX are present in a ratio of about 1:4 to 4:1, or about 1:1. In another embodiment, the ratio of PDX:GOS can be between about 5:1 and 1:5. In yet another embodiment, the ratio of PDX:GOS can be between about 1:3 and 3:1. In a particular embodiment, the ratio of PDX to GOS can be about 5:5. In another particular embodiment, the ratio of PDX to GOS can be about 8:2.

In some embodiments, the amount of GOS in the nutritional composition may be from about 0.1 g/100 kcal to about 1.0 g/100 kcal. In another embodiment, the amount of GOS in the nutritional composition may be from about 0.1 g/100 kcal to about 0.5 g/100 kcal. The amount of PDX in the nutritional composition may, in some embodiments, be within the range of from about 0.1 g/100 kcal to about 0.5 g/100 kcal. In other embodiments, the amount of PDX may be about 0.3 g/100 kcal.

In a particular embodiment, GOS and PDX are supplemented into the nutritional composition in a total amount of about at least about 0.2 g/100 kcal and can be about 0.2 g/100 kcal to about 1.5 g/100 kcal. In some embodiments, the nutritional composition may comprise GOS and PDX in a total amount of from about 0.6 to about 0.8 g/100 kcal.

In some embodiments the nutritional composition comprises a probiotic, and more particularly, *Lactobacillus rhamnosus* GG (LGG, ATCC number 53103). Other probiotics useful in the present nutritional compositions include, but are not limited to, *Bifidobacterium* species (e.g., *Bifidobacterium animalis, Bifidobacterium breve* B-3, and *Bifidobacterium longum* subsp. *infantis* M-63), and combinations thereof.

In certain embodiments, one or more of the probiotics can be present in the nutritional composition in an amount of from about $1 \times 10^4$ cfu/100 kcal to about $1.5 \times 10^{10}$ cfu/100 kcal or about $1 \times 10^4$ cell equivalent/100 kcal to about $1.5 \times 10^{10}$ cell equivalent/100 kcal. In other embodiments, the nutritional composition comprises one or more of the probiotics in an amount of from about $1 \times 10^6$ cfu/100 kcal to about $1 \times 10^9$ cfu/100 kcal or about $1 \times 10^6$ cell equivalent/100 kcal to about $1.5 \times 10^9$ cell equivalent/100 kcal. Still, in certain embodiments, the nutritional composition may include one or more of the probiotics in an amount of from about $1 \times 10^7$ cfu/100 kcal to about $1 \times 10^8$ cfu/100 kcal or about $1 \times 10^7$ cell equivalent/100 kcal to about $1.5 \times 10^8$ cell equivalent/100 kcal. The probiotic may be either non-viable or viable.

In some embodiments, rather than (or in addition to) adding a probiotic to the composition, probiotic functionality is provided by including a culture supernatant from a late-exponential growth phase of a probiotic batch-cultivation process, as disclosed in international published application no. WO 2013/142403, which is hereby incorporated by reference in its entirety. Without wishing to be bound by theory, it is believed that the activity of the culture supernatant can be attributed to the mixture of components (including proteinaceous materials, and possibly including (exo)polysaccharide materials) released into the culture medium at a late stage of the exponential (or "log") phase of batch cultivation of the probiotic. The term "culture supernatant" as used herein, includes the mixture of components found in the culture medium. The stages recognized in batch cultivation of bacteria are known to the skilled person. These are the "lag," the "log" ("logarithmic" or "exponential"), the "stationary" and the "death" (or "logarithmic decline") phases. In all phases during which live bacteria are present, the bacteria metabolize nutrients from the media, and secrete (exert, release) materials into the culture medium. The composition of the secreted material at a given point in time of the growth stages is not generally predictable.

In an embodiment, a culture supernatant is obtainable by a process comprising the steps of (a) subjecting a probiotic such as LGG to cultivation in a suitable culture medium using a batch process; (b) harvesting the culture supernatant at a late exponential growth phase of the cultivation step, which phase is defined with reference to the second half of the time between the lag phase and the stationary phase of the batch-cultivation process; (c) optionally removing low molecular weight constituents from the supernatant so as to retain molecular weight constituents above 5-6 kiloDaltons (kDa); (d) removing liquid contents from the culture supernatant so as to obtain the composition.

The culture supernatant may comprise secreted materials that are harvested from a late exponential phase. The late exponential phase occurs in time after the mid exponential phase (which is halftime of the duration of the exponential phase, hence the reference to the late exponential phase as being the second half of the time between the lag phase and the stationary phase). In particular, the term "late exponential phase" is used herein with reference to the latter quarter portion of the time between the lag phase and the stationary phase of the probiotic (e.g., LGG) batch-cultivation process. In some embodiments, the culture supernatant is harvested at a point in time of 75% to 85% of the duration of the exponential phase, and may be harvested at about ⅚ of the time elapsed in the exponential phase.

In some embodiments, a soluble mediator preparation is prepared from the culture supernatant as described below. Furthermore, preparation of an LGG soluble mediator preparation is described in US 20130251829 and US 20110217402, each of which is incorporated by reference in its entirety. The stages recognized in batch cultivation of bacteria are known to the skilled person. These are the "lag," the "log" ("logarithmic" or "exponential"), the "stationary" and the "death" (or "logarithmic decline") phases. In all phases during which live bacteria are present, the bacteria metabolize nutrients from the media, and secrete (exert, release) materials into the culture medium. The composition of the secreted material at a given point in time of the growth stages is not generally predictable.

In certain embodiments, the soluble mediator preparation is obtainable by a process comprising the steps of (a) subjecting a probiotic such as LGG to cultivation in a suitable culture medium using a batch process; (b) harvesting a culture supernatant at a late exponential growth phase of the cultivation step, which phase is defined with reference to the second half of the time between the lag phase and the stationary phase of the batch-cultivation process; (c) optionally removing low molecular weight constituents from the supernatant so as to retain molecular weight constituents above 5-6 kiloDaltons (kDa); (d) removal of any remaining cells using 0.22 µm sterile filtration to provide the soluble mediator preparation; (e) removing liquid contents from the soluble mediator preparation so as to obtain the composition.

In certain embodiments, secreted materials are harvested from a late exponential phase. The late exponential phase occurs in time after the mid exponential phase (which is halftime of the duration of the exponential phase, hence the reference to the late exponential phase as being the second half of the time between the lag phase and the stationary phase). In particular, the term "late exponential phase" is used herein with reference to the latter quarter portion of the time between the lag phase and the stationary phase of the LGG batch-cultivation process. In a preferred embodiment of the present disclosure and embodiments thereof, harvesting of the culture supernatant is at a point in time of 75% to 85% of the duration of the exponential phase, and most preferably is at about ⅚ of the time elapsed in the exponential phase.

The term "cultivation" or "culturing" refers to the propagation of micro-organisms, in this case LGG, on or in a suitable medium. Such a culture medium can be of a variety of kinds, and is particularly a liquid broth, as customary in the art. A preferred broth, e.g., is MRS broth as generally used for the cultivation of lactobacilli. MRS broth generally comprises polysorbate, acetate, magnesium and manganese, which are known to act as special growth factors for lactobacilli, as well as a rich nutrient base. A typical composition comprises (amounts in g/liter): peptone from casein 10.0; meat extract 8.0; yeast extract 4.0; D(+)-glucose 20.0; dipotassium hydrogen phosphate 2.0; Tween® 80 1.0; triammonium citrate 2.0; sodium acetate 5.0; magnesium sulfate 0.2; manganese sulfate 0.04.

In certain embodiments, the soluble mediator preparation is incorporated into an infant formula or other nutritional composition. The harvesting of secreted bacterial products brings about a problem that the culture media cannot easily be deprived of undesired components. This specifically relates to nutritional products for relatively vulnerable subjects, such as infant formula or clinical nutrition. This problem is not incurred if specific components from a culture supernatant are first isolated, purified, and then applied in a nutritional product. However, it is desired to make use of a more complete culture supernatant. This would serve to provide a soluble mediator composition better reflecting the natural action of the probiotic (e.g. LGG).

Accordingly, it is desired to ensure that the composition harvested from LGG cultivation does not contain components (as may present in the culture medium) that are not desired, or generally accepted, in such formula. With reference to polysorbate regularly present in MRS broth, media for the culturing of bacteria may include an emulsifying non-ionic surfactant, e.g. on the basis of polyethoxylated sorbitan and oleic acid (typically available as Tween® polysorbates, such as Tween® 80). Whilst these surfactants are frequently found in food products, e.g. ice cream, and are generally recognized as safe, they are not in all jurisdictions considered desirable, or even acceptable for use in nutritional products for relatively vulnerable subjects, such as infant formula or clinical nutrition.

Therefore, in some embodiments, a preferred culture medium of the disclosure is devoid of polysorbates such as Tween 80. In a preferred embodiment of the disclosure and/or embodiments thereof the culture medium may comprise an oily ingredient selected from the group consisting of oleic acid, linseed oil, olive oil, rape seed oil, sunflower oil and mixtures thereof. It will be understood that the full benefit of the oily ingredient is attained if the presence of a polysorbate surfactant is essentially or entirely avoided.

More particularly, in certain embodiments, an MRS medium is devoid of polysorbates. Also preferably medium comprises, in addition to one or more of the foregoing oils, peptone (typically 0-10 g/L, especially 0.1-10 g/L), meat extract (typically 0-8 g/L, especially 0.1-8 g/L), yeast extract (typically 4-50 g/L), D(+) glucose (typically 20-70 g/L), dipotassium hydrogen phosphate (typically 2-4 g/L), sodium acetate trihydrate (typically 4-5 g/L), triammonium citrate (typically 2-4 g/L), magnesium sulfate heptahydrate (typically 0.2-0.4 g/L) and/or manganous sulfate tetrahydrate (typically 0.05-0.08 g/L).

The culturing is generally performed at a temperature of 20° C. to 45° C., more particularly at 35° C. to 40° C., and more particularly at 37° C. In some embodiments, the culture has a neutral pH, such as a pH of between pH 5 and pH 7, preferably pH 6.

In some embodiments, the time point during cultivation for harvesting the culture supernatant, i.e., in the aforementioned late exponential phase, can be determined, e.g. based on the OD600 nm and glucose concentration. OD600 refers to the optical density at 600 nm, which is a known density measurement that directly correlates with the bacterial concentration in the culture medium.

The culture supernatant can be harvested by any known technique for the separation of culture supernatant from a bacterial culture. Such techniques are known in the art and include, e.g., centrifugation, filtration, sedimentation, and the like. In some embodiments, LGG cells are removed from the culture supernatant using 0.22 μm sterile filtration in order to produce the soluble mediator preparation. The probiotic soluble mediator preparation thus obtained may be used immediately, or be stored for future use. In the latter case, the probiotic soluble mediator preparation will generally be refrigerated, frozen or lyophilized. The probiotic soluble mediator preparation may be concentrated or diluted, as desired.

The soluble mediator preparation is believed to contain a mixture of amino acids, oligo- and polypeptides, and proteins, of various molecular weights. The composition is further believed to contain polysaccharide structures and/or nucleotides.

In some embodiments, the soluble mediator preparation of the present disclosure excludes lower molecular weight components, generally below 6 kDa, or even below 5 kDa. In these and other embodiments, the soluble mediator preparation does not include lactic acid and/or lactate salts. These lower molecular weight components can be removed, for example, by filtration or column chromatography. In some embodiments, the culture supernatant is subjected to ultrafiltration with a 5 kDa membrane in order to retain constituents over 5 kDa. In other embodiments, the culture supernatant is desalted using column chromatography to retain constituents over 6 kDa.

The soluble mediator preparation of the present disclosure can be formulated in various ways for administration to pediatric subjects. For example, the soluble mediator preparation can be used as such, e.g. incorporated into capsules for oral administration, or in a liquid nutritional composition such as a drink, or it can be processed before further use. Such processing generally involves separating the compounds from the generally liquid continuous phase of the supernatant. This preferably is done by a drying method, such as spray-drying or freeze-drying (lyophilization). In a preferred embodiment of the spray-drying method, a carrier material will be added before spray-drying, e.g., maltodextrin DE29.

Probiotic bacteria soluble mediator preparations, such as the LGG soluble mediator preparation disclosed herein, advantageously possess gut barrier enhancing activity by promoting gut barrier regeneration, gut barrier maturation and/or adaptation, gut barrier resistance and/or gut barrier function. The present LGG soluble mediator preparation may accordingly be particularly useful in treating subjects, particularly pediatric subjects, with impaired gut barrier function, such as short bowel syndrome or NEC. The soluble mediator preparation may be particularly useful for infants and premature infants having impaired gut barrier function and/or short bowel syndrome.

Probiotic bacteria soluble mediator preparation, such as the LGG soluble mediator preparation of the present disclosure, also advantageously reduce visceral pain sensitivity in subjects, particularly pediatric subjects experiencing gastrointestinal pain, food intolerance, allergic or non-allergic inflammation, colic, IBS, and infections.

The nutritional composition of the disclosure may contain a source of long chain polyunsaturated fatty acid (LCPUFA), e.g., docosahexaenoic acid (DHA). Other suitable LCPUFAs include, but are not limited to, linoleic (18:2 n-6), γ-linolenic (18:3 n-6), dihomo-γ-linolenic (20:3 n-6) acids in the n-6 pathway, α-linolenic (18:3 n-3), stearidonic (18:4 n-3), eicosatetraenoic (20:4 n-3), eicosapentaenoic (20:5 n-3), and docosapentaenoic (22:6 n-3) and arachidonic acid (ARA).

In certain embodiments the amount of LCPUFA in the nutritional composition is at least about 5 mg/100 Kcal, and may vary from about 5 mg/100 Kcal to about 100 mg/100 Kcal, more preferably from about 10 mg/100 Kcal to about 50 mg/100 Kcal.

In certain embodiments, the amount of DHA in the nutritional composition is at least about 17 mg/100 Kcals, and can vary from about 5 mg/100 Kcal to about 75 mg/100 Kcal, or from about 10 mg/100 Kcal to about 50 mg/100 Kcal.

In an embodiment, especially if the nutritional composition is an infant formula, the nutritional composition is supplemented with both DHA and ARA. In this embodiment, the weight ratio of ARA:DHA may be between about 1:3 and about 9:1. In a particular embodiment, the ratio of ARA:DHA is from about 1:2 to about 4:1.

If included, the source of DHA and/or ARA may be any source known in the art such as marine oil, fish oil, single cell oil, egg yolk lipid, and brain lipid. In some embodiments, the DHA and ARA are sourced from single cell Martek oils, DHASCO® and ARASCO®, or variations thereof. The DHA and ARA can be in natural form, provided that the remainder of the LCPUFA source does not result in any substantial deleterious effect on the subject. Alternatively, the DHA and ARA can be used in refined form.

In an embodiment, sources of DHA and ARA are single cell oils as taught in U.S. Pat. Nos. 5,374,657; 5,550,156; and 5,397,591, the disclosures of which are incorporated herein in their entirety by reference. Nevertheless, the present disclosure is not limited to only such oils.

The nutritional composition may also comprise a source of beta-glucan. Glucans are polysaccharides, specifically polymers of glucose, which are naturally occurring and may be found in cell walls of bacteria, yeast, fungi, and plants. Beta glucans β-glucans) are themselves a diverse subset of glucose polymers, which are made up of chains of glucose monomers linked together via beta-type glycosidic bonds to form complex carbohydrates.

β-1,3-glucans are carbohydrate polymers purified from, for example, yeast, mushroom, bacteria, algae, or cereals. The chemical structure of β-1,3-glucan depends on the source of the β-1,3-glucan. Moreover, various physiochemical parameters, such as solubility, primary structure, molecular weight, and branching, play a role in biological activities of β-1,3-glucans. (Yadomae T., Structure and biological activities of fungal beta-1,3-glucans. Yakugaku Zasshi. 2000; 120:413-431.)

β-1,3-glucans are naturally occurring polysaccharides, with or without β-1,6-glucose side chains that are found in the cell walls of a variety of plants, yeasts, fungi and bacteria. β-1,3;1,6-glucans are those containing glucose units with (1,3) links having side chains attached at the (1,6) position(s). β-1,3;1,6 glucans are a heterogeneous group of glucose polymers that share structural commonalities, including a backbone of straight chain glucose units linked by a β-1,3 bond with β-1,6-linked glucose branches extending from this backbone. While this is the basic structure for the presently described class of β-glucans, some variations may exist. For example, certain yeast β-glucans have additional regions of β(1,3) branching extending from the β(1,6) branches, which add further complexity to their respective structures.

β-glucans derived from baker's yeast, *Saccharomyces cerevisiae*, are made up of chains of D-glucose molecules connected at the 1 and 3 positions, having side chains of glucose attached at the 1 and 6 positions. Yeast-derived β-glucan is an insoluble, fiber-like, complex sugar having the general structure of a linear chain of glucose units with a β-1,3 backbone interspersed with β-1,6 side chains that are generally 6-8 glucose units in length. More specifically, β-glucan derived from baker's yeast is poly-(1,6)-β-D-glucopyranosyl-(1,3)-β-D-glucopyranose.

Furthermore, β-glucans are well tolerated and do not produce or cause excess gas, abdominal distension, bloating or diarrhea in pediatric subjects. Addition of β-glucan to a nutritional composition for a pediatric subject, such as an infant formula, a growing-up milk or another children's nutritional product, will improve the pediatric subject's immune response by increasing resistance against invading pathogens and therefore maintaining or improving overall health.

In some embodiments, the amount of β-glucan in the nutritional composition is between about 3 mg and about 17 mg per 100 Kcal. In another embodiment the amount of β-glucan is between about 6 mg and about 17 mg per 100 Kcal.

In a particular embodiment, a nutritional composition comprises per 100 kcal: (i) between about 1 g and about 7 g of a protein source, (ii) between about 1 g and about 10 g of a lipid source, (iii) between about 6 g and about 22 g of a carbohydrate source, (iv) between about 0.005 g and about 1 g of a human milk oligosaccharide, (v) between about 0.1 g and 1.0 g of a galacto-oligosaccharide, (vi) between about 0.1 g and about 0.5 g of polydextrose, and (vii) between about $1 \times 10^5$ cfu/100 kcals to about $1.5 \times 10^{10}$ cfu/100 kcals of *Lactobacillus rhamnosus* GG or about $1 \times 10^5$ cell equivalent/100 kcals to about $1.5 \times 10^{10}$ cell equivalent/100 kcals of dry composition of *Lactobacillus rhamnosus* GG. In some embodiments, the nutritional composition comprises the culture supernatant from about 0.015 g per 100 kcal to about 1.5 g per 100 kcal.

The disclosed nutritional composition(s) may be provided in any form known in the art, such as a powder, a gel, a suspension, a paste, a solid, a liquid, a liquid concentrate, a reconstitutable powdered milk substitute or a ready-to-use product. The nutritional composition may, in certain embodiments, comprise a nutritional supplement, children's nutritional product, infant formula, human milk fortifier, growing-up milk or any other nutritional composition designed for a pediatric subject. Nutritional compositions of the present disclosure include, for example, orally-ingestible, health-promoting substances including, for example, foods, beverages, tablets, capsules and powders. Moreover, the nutritional composition of the present disclosure may be standardized to a specific caloric content, it may be provided as a ready-to-use product, or it may be provided in a concentrated form. In some embodiments, the nutritional composition is in powder form with a particle size in the range of 5 μm to 1500 more preferably in the range of 10 μm to 1000 μm, and even more preferably in the range of 50 μm to 300 μm.

In some embodiments, the nutritional composition is an infant formula suitable for infants ranging in age from 0 to 12 months, from 0 to 3 months, 0 to 6 months or 6 to 12 months. In other embodiments, the disclosure provides a fortified milk-based growing-up milk designed for children ages 1-3 years and/or 4-6 years, wherein the growing-up milk supports growth and development and life-long health.

As noted, the nutritional composition(s) of the disclosure may comprise a protein source. The protein source can be any used in the art, e.g., nonfat milk, whey protein, casein, soy protein, hydrolyzed protein, amino acids, and the like. Bovine milk protein sources useful in practicing the present disclosure include, but are not limited to, milk protein powders, milk protein concentrates, milk protein isolates, nonfat milk solids, nonfat milk, nonfat dry milk, whey protein, whey protein isolates, whey protein concentrates, sweet whey, acid whey, casein, acid casein, caseinate (e.g. sodium caseinate, sodium calcium caseinate, calcium caseinate) and any combinations thereof.

In one embodiment, the hydrolysates of the present disclosure are provided without an additional protein source. In other embodiments, the proteins are provided as a combination of both intact proteins and the hydrolyzed proteins disclosed herein. In still other embodiments, the hydrolysates of the present disclosure are provided in combination with amino acids. In yet another embodiment, the hydrolysates of the present disclosure may be supplemented with glutamine-containing peptides.

In a particular embodiment of the nutritional composition, the whey:casein ratio of the protein source is similar to that found in human breast milk. In an embodiment, the protein source comprises from about 40% to about 90% whey protein and from about 10% to about 60% casein.

In some embodiments, the nutritional composition comprises between about 1 g and about 7 g of a protein source per 100 kcal. In other embodiments, the nutritional composition comprises between about 3.5 g and about 4.5 g of protein per 100 kcal.

In some embodiments, the protein equivalent source comprises a hydrolyzed protein, which includes partially hydrolyzed protein and extensively hydrolyzed protein, such as casein. In some embodiments, the protein equivalent source comprises a hydrolyzed protein including peptides having a molar mass distribution of greater than 500 Daltons. In some embodiments, the hydrolyzed protein comprises peptides, wherein at least 80% of the peptide have a molar mass distribution in the range of from about 500 Daltons to about 2,500 Daltons. Still, in some embodiments, the hydrolyzed protein comprises peptides wherein at least 80% of the peptides have a molar mass distribution range of from about 500 Daltons to about 5,000 Daltons.

In some embodiments, the nutritional composition comprises between about 1 g and about 7 g of a protein equivalent source per 100 Kcal. In other embodiments, the nutritional composition comprises between about 3.5 g and about 4.5 g of protein equivalent source per 100 Kcal.

In certain embodiments, the protein equivalent source comprises amino acids and is substantially free of whole, intact protein. In certain embodiments, the protein equivalent source includes from about 10% to about 90% w/w of essential amino acids based on the total amino acids included in the protein equivalent source. In certain embodiments, the protein equivalent source includes from about 25% to about 75% w/w of essential amino acids based on the total amino acids included in the protein equivalent source. In some embodiments, the protein equivalent source includes from about 40% to about 60% of essential amino acids based on the total amino acids included in the protein equivalent source.

In some embodiments, the protein equivalent source includes non-essential amino acids. In certain embodiments, the protein equivalent source includes from about 10% to about 90% w/w of non-essential amino acids based on the total amino acids included in the protein equivalent source. In certain embodiments, the protein equivalent source includes from about 25% to about 75% w/w of non-essential amino acids based on the total amino acids included in the protein equivalent source. In some embodiments, the protein equivalent source includes from about 40% to about 60% w/w of non-essential amino acids based on the total amino acids included in the protein equivalent source.

In some embodiments, the protein equivalent source includes leucine. In some embodiments, the protein equivalent source includes from about 2% to about 15% w/w leucine per the total amount of amino acids included in the protein equivalent source. In some embodiments, the protein equivalent source includes from about 4% to about 10% w/w leucine per the total amount of amino acids included in the protein equivalent source.

In some embodiments, the protein equivalent source includes lysine. In some embodiments, the protein equivalent source includes from about 2% to about 10% w/w lysine per the total amino acids included in the protein equivalent source. In some embodiments, the protein equivalent source includes from about 4% to about 8% w/w lysine per the total amino acids in the protein equivalent source.

In some embodiments, the protein equivalent source includes valine. In some embodiments, the protein equivalent source includes from about 2% to about 15% w/w valine per the total amino acids included in the protein equivalent source. In some embodiments, the protein equivalent source includes from about 4% to about 10% w/w valine per the total amino acids in the protein equivalent source.

In some embodiments, the protein equivalent source includes isoleucine. In some embodiments, the protein equivalent source includes from about 1% to about 8% w/w isoleucine per the total amino acids included in the protein equivalent source. In some embodiments, the protein equivalent source includes from about 3% to about 7% w/w isoleucine per the total amino acids in the protein equivalent source.

In some embodiments, the protein equivalent source includes threonine. In some embodiments, the protein equivalent source includes from about 1% to about 8% w/w threonine per the total amino acids included in the protein equivalent source. In some embodiments, the protein equivalent source includes from about 3% to about 7% w/w threonine per the total amino acids in the protein equivalent source.

In some embodiments, the protein equivalent source includes tyrosine. In some embodiments, the protein equivalent source includes from about 1% to about 8% w/w tyrosine per the total amino acids included in the protein equivalent source. In some embodiments, the protein equivalent source includes from about 3% to about 7% w/w tyrosine per the total amino acids in the protein equivalent source.

In some embodiments, the protein equivalent source includes phenylalanine. In some embodiments, the protein equivalent source includes from about 1% to about 8% w/w phenylalanine per the total amino acids included in the protein equivalent source. In some embodiments, the protein equivalent source includes from about 3% to about 7% w/w phenylalanine per the total amino acids in the protein equivalent source.

In some embodiments, the protein equivalent source includes histidine. In some embodiments, the protein equivalent source includes from about 0.5% to about 4% w/w histidine per the total amino acids included in the protein equivalent source. In some embodiments, the protein equivalent source includes from about 1.5% to about 3.5% w/w histidine per the total amino acids in the protein equivalent source.

In some embodiments, the protein equivalent source includes cysteine. In some embodiments, the protein equivalent source includes from about 0.5% to about 4% w/w cysteine per the total amino acids included in the protein equivalent source. In some embodiments, the protein equivalent source includes from about 1.5% to about 3.5% w/w cysteine per the total amino acids in the protein equivalent source.

In some embodiments, the protein equivalent source includes tryptophan. In some embodiments, the protein equivalent source includes from about 0.5% to about 4% w/w tryptophan per the total amino acids included in the protein equivalent source. In some embodiments, the protein equivalent source includes from about 1.5% to about 3.5% w/w tryptophan per the total amino acids in the protein equivalent source.

In some embodiments, the protein equivalent source includes methionine. In some embodiments, the protein equivalent source includes from about 0.5% to about 4% w/w methionine per the total amino acids included in the protein equivalent source. In some embodiments, the protein equivalent source includes from about 1.5% to about 3.5% w/w methionine per the total amino acids in the protein equivalent source.

In some embodiments, the protein equivalent source includes aspartic acid. In some embodiments, the protein equivalent source includes from about 7% to about 20% w/w aspartic acid per the total amino acids included in the protein equivalent source. In some embodiments, the protein equivalent source includes from about 10% to about 17% w/w aspartic acid per the total amino acids in the protein equivalent source.

In some embodiments, the protein equivalent source includes proline. In some embodiments, the protein equivalent source includes from about 5% to about 12% w/w proline per the total amino acids included in the protein equivalent source. In some embodiments, the protein equivalent source includes from about 7% to about 10% w/w proline per the total amino acids in the protein equivalent source.

In some embodiments, the protein equivalent source includes alanine. In some embodiments, the protein equivalent source includes from about 3% to about 10% w/w alanine per the total amino acids included in the protein equivalent source. In some embodiments, the protein equivalent source includes from about 5% to about 8% w/w alanine per the total amino acids in the protein equivalent source.

In some embodiments, the protein equivalent source includes glutamate. In some embodiments, the protein equivalent source includes from about 1.5% to about 8% w/w glutamate per the total amino acids included in the protein equivalent source. In some embodiments, the protein equivalent source includes from about 3% to about 6% w/w glutamate per the total amino acids in the protein equivalent source.

In some embodiments, the protein equivalent source includes serine. In some embodiments, the protein equivalent source includes from about 1.5% to about 8% w/w serine per the total amino acids included in the protein equivalent source. In some embodiments, the protein equivalent source includes from about 3% to about 5% w/w serine per the total amino acids in the protein equivalent source.

In some embodiments, the protein equivalent source includes arginine. In some embodiments, the protein equivalent source includes from about 2% to about 8% w/w arginine per the total amino acids included in the protein equivalent source. In some embodiments, the protein equivalent source includes from about 3.5% to about 6% w/w arginine per the total amino acids in the protein equivalent source.

In some embodiments, the protein equivalent source includes glycine. In some embodiments, the protein equivalent source includes from about 0.5% to about 6% w/w glycine per the total amino acids included in the protein equivalent source. In some embodiments, the protein equivalent source includes from about 1.5% to about 3.5% w/w glycine per the total amino acids in the protein equivalent source.

In some embodiments, the nutritional composition comprises between about 1 g and about 7 g of a protein equivalent source per 100 Kcal. In other embodiments, the nutritional composition comprises between about 3.5 g and about 4.5 g of protein equivalent source per 100 Kcal.

In some embodiments, the nutritional composition comprises between about 0.5 g/100 Kcal and about 2.5 g/100 Kcal of essential amino acids. In certain embodiments, the nutritional composition comprises between about 1.3 g/100 Kcal to about 1.6 Kcal of essential amino acids.

In some embodiments, the nutritional composition comprises between about 0.5 g/100 Kcal and about 2.5 g/100 Kcal of essential amino acids. In certain embodiments, the nutritional composition comprises between about 1.3 g/100 Kcal to about 1.6 Kcal of non-essential amino acids.

In some embodiments, the nutritional composition comprises from about 0.2 g/100 Kcal to about 0.5 g/100 Kcal of leucine. In some embodiments, the nutritional composition comprises from about 0.1 g/100 Kcal to about 0.4 g/100 Kcal of lysine. In some embodiments, the nutritional composition comprises from about 0.1 g/100 Kcal to about 0.4 g/100 Kcal of valine. In some embodiments, the nutritional composition comprises from about 0.08 g/100 Kcal to about 0.23 g/100 Kcal of isoleucine. In some embodiments, the nutritional composition comprises from about 0.08 g/100 Kcal to about 0.20 g/100 Kcal of threonine. In some embodiments, the nutritional composition comprises from about 0.10 g/100 Kcal to about 0.15 g/100 Kcal of tyrosine. In some embodiments, the nutritional composition comprises from about 0.05 g/100 Kcal to about 0.15 g/100 Kcal of phenylalanine. In some embodiments, the nutritional composition comprises from about 0.01 g/100 Kcal to about 0.09 g/100 Kcal of histidine. In some embodiments, the nutritional composition comprises from about 0.02 g/100 Kcal to about 0.08 g/100 Kcal of cysteine. In some embodiments, the nutritional composition comprises from about 0.02 g/100 Kcal to about 0.08 g/100 Kcal of tryptophan. In some embodiments, the nutritional composition comprises from about 0.02 g/100 Kcal to about 0.08 g/100 Kcal of methionine.

In some embodiments, the nutritional composition comprises from about 0.2 g/100 Kcal to about 0.7 g/100 Kcal of aspartic acid. In some embodiments, the nutritional composition comprises from about 0.1 g/100 Kcal to about 0.4 g/100 Kcal of proline. In some embodiments, the nutritional composition comprises from about 0.1 g/100 Kcal to about 0.3 g/100 Kcal of alanine. In some embodiments, the nutritional composition comprises from about 0.08 g/100 Kcal to about 0.25 g/100 Kcal of glutamate. In some embodiments, the nutritional composition comprises from about 0.08 g/100 Kcal to about 0.2 g/100 Kcal of serine. In some embodiments, the nutritional composition comprises from about 0.08 g/100 Kcal to about 0.15 g/100 Kcal of arginine. In some embodiments, the nutritional composition comprises from about 0.02 g/100 Kcal to about 0.08 g/100 Kcal of glycine.

The nutritional composition(s) of the present disclosure including the protein equivalent source, may be administered in one or more doses daily. Any orally acceptable dosage form is contemplated by the present disclosure. Examples of such dosage forms include, but are not limited to pills, tablets, capsules, soft-gels, liquids, liquid concentrates, powders, elixirs, solutions, suspensions, emulsions, lozenges, beads, cachets, and combinations thereof.

In some embodiments, the protein equivalent source may provide from about 5% to about 20% of the total calories for the nutritional composition. In some embodiments, the protein equivalent source may provide from about 8% to about 12% of the total calories for the nutritional composition.

Carbohydrate sources can be any used in the art, e.g., lactose, glucose, fructose, corn syrup solids, maltodextrins, sucrose, starch, rice syrup solids, and the like. The amount of carbohydrate in the nutritional composition typically can vary from between about 5 g and about 25 g/100 kcal. In some embodiments, the nutritional composition comprises between about 3 g and about 8 g of a carbohydrate source.

Carbohydrate sources can be any used in the art, e.g., lactose, glucose, fructose, corn syrup solids, maltodextrins, sucrose, starch, rice syrup solids, and the like. The amount of carbohydrate in the nutritional composition typically can vary from between about 5 g and about 25 g/100 Kcal. In some embodiments, the amount of carbohydrate is between about 6 g and about 22 g/100 Kcal. In other embodiments, the amount of carbohydrate is between about 12 g and about 14 g/100 Kcal. In some embodiments, corn syrup solids are preferred. Moreover, hydrolyzed, partially hydrolyzed, and/or extensively hydrolyzed carbohydrates may be desirable for inclusion in the nutritional composition due to their easy digestibility. Specifically, hydrolyzed carbohydrates are less likely to contain allergenic epitopes.

Suitable fat or lipid sources for the nutritional composition of the present disclosure may be any known or used in the art, including but not limited to, animal sources, e.g., milk fat, butter, butter fat, egg yolk lipid; marine sources, such as fish oils, marine oils, single cell oils; vegetable and plant oils, such as corn oil, canola oil, sunflower oil, soybean oil, palm olein oil, coconut oil, high oleic sunflower oil, evening primrose oil, rapeseed oil, olive oil, flaxseed (linseed) oil, cottonseed oil, high oleic safflower oil, palm stearin, palm kernel oil, wheat germ oil; medium chain triglyceride oils and emulsions and esters of fatty acids; and any combinations thereof.

In some embodiments, the nutritional composition comprises between about 1 g and about 10 g per 100 kcal of a lipid source. In some embodiments, the nutritional composition comprises between about 2 g/100 Kcal to about 7 g/100 Kcal of a fat source. In other embodiments the fat source may be present in an amount from about 2.5 g/100 Kcal to about 6 g/100 Kcal. In still other embodiments, the fat source may be present in the nutritional composition in an amount from about 3 g/100 Kcal to about 4 g/100 Kcal. In some embodiments, the nutritional composition comprises between about 3 g and about 8 g per 100 kcal of a lipid source. In some embodiments, the nutritional composition comprises between about 5 and about 6 g per 100 kcal of a lipid source.

In some embodiments, the fat or lipid source comprises from about 10% to about 35% palm oil per the total amount of fat or lipid. In some embodiments, the fat or lipid source comprises from about 15% to about 30% palm oil per the total amount of fat or lipid. Yet in other embodiments, the fat or lipid source may comprise from about 18% to about 25% palm oil per the total amount of fat or lipid.

In certain embodiments, the fat or lipid source may be formulated to include from about 2% to about 16% soybean oil based on the total amount of fat or lipid. In some embodiments, the fat or lipid source may be formulated to include from about 4% to about 12% soybean oil based on the total amount of fat or lipid. In some embodiments, the fat or lipid source may be formulated to include from about 6% to about 10% soybean oil based on the total amount of fat or lipid.

In certain embodiments, the fat or lipid source may be formulated to include from about 2% to about 16% coconut oil based on the total amount of fat or lipid. In some embodiments, the fat or lipid source may be formulated to include from about 4% to about 12% coconut oil based on the total amount of fat or lipid. In some embodiments, the fat or lipid source may be formulated to include from about 6% to about 10% coconut oil based on the total amount of fat or lipid.

In certain embodiments, the fat or lipid source may be formulated to include from about 2% to about 16% sunflower oil based on the total amount of fat or lipid. In some embodiments, the fat or lipid source may be formulated to include from about 4% to about 12% sunflower oil based on the total amount of fat or lipid. In some embodiments, the fat or lipid source may be formulated to include from about 6% to about 10% sunflower oil based on the total amount of fat or lipid.

In some embodiments, the oils, i.e. sunflower oil, soybean oil, sunflower oil, palm oil, etc. are meant to cover fortified versions of such oils known in the art. For example, in certain embodiments, the use of sunflower oil may include high oleic sunflower oil. In other examples, the use of such oils may be fortified with certain fatty acids, as known in the art, and may be used in the fat or lipid source disclosed herein.

In some embodiments, the fat or lipid source includes an oil blend including sunflower oil, medium chain triglyceride oil, and soybean oil. In some embodiments, the fat or lipid source includes a ratio of sunflower oil to medium chain triglyceride oil of about 1:1 to about 2:1. In certain other embodiments, the fat or lipid source includes a ratio of sunflower oil to soybean oil of from about 1:1 to about 2:1. In still other embodiments, the fat or lipid source may include a ratio of medium chain triglyceride oil to soybean oil of from about 1:1 to about 2:1.

In certain embodiments the fat or lipid source may comprise from about 15% to about 50% w/w sunflower oil based on the total fat or lipid content. In certain embodiments, the fat or lipid source includes from about 25% to about 40% w/w sunflower oil based on the total fat or lipid content. In some embodiments, the fat or lipid source comprises from about 30% to about 35% w/w sunflower oil based on the total fat or lipid content.

In certain embodiments the fat or lipid source may comprise from about 15% to about 50% w/w medium chain triglyceride oil based on the total fat or lipid content. In certain embodiments, the fat or lipid source includes from about 25% to about 40% w/w medium chain triglyceride oil based on the total fat or lipid content. In some embodiments, the fat or lipid source comprises from about 30% to about 35% w/w medium chain triglyceride oil based on the total fat or lipid content.

In certain embodiments the fat or lipid source may comprise from about 15% to about 50% w/w soybean oil based on the total fat or lipid content. In certain embodiments, the fat or lipid source includes from about 25% to about 40% w/w soybean oil based on the total fat or lipid content. In some embodiments, the fat or lipid source comprises from about 30% to about 35% w/w soybean oil based on the total fat or lipid content.

In some embodiments, the nutritional composition comprises from about 1 g/100 Kcal to about 3 g/100 Kcal of sunflower oil. In some embodiments, the nutritional composition comprises from about 1.3 g/100 Kcal to about 2.5 g/100 Kcal of sunflower oil. In still other embodiments, the nutritional composition comprises from about 1.7 g/100 Kcal to about 2.1 g/100 Kcal of sunflower oil. The sunflower oil as described herein may, in some embodiments, include high oleic sunflower oil.

In certain embodiments, the nutritional composition if formulated to include from about 1 g/100 Kcal to about 2.5 g/100 Kcal of medium chain triglyceride oil. In other embodiments, the nutritional composition includes from about 1.3 g/100 Kcal to about 2.1 g/100 Kcal of medium chain triglyceride oil. Still in further embodiments, the nutritional composition includes from about 1.6 g/100 Kcal to about 1.9 g/100 Kcal of medium chain triglyceride oil.

In some embodiments, the nutritional composition may be formulated to include from about 1 g/100 Kcal to about 2.3 g/100 Kcal of soybean oil. In certain embodiments, the nutritional composition may be formulated to include from about 1.2 g/100 Kcal to about 2 g/100 Kcal of soybean oil. Still in certain embodiments, the nutritional composition may be formulated to include from about 1.5 g/100 Kcal to about 1.8 g/100 Kcal of soybean oil.

In some embodiments, the term "sunflower oil", "medium chain triglyceride oil", and "soybean oil" are meant to cover fortified versions of such oils known in the art. For example, in certain embodiments, the use of sunflower oil may include high oleic sunflower oil. In other examples, the use of such oils may be fortified with certain fatty acids, as known in the art, and may be used in the fat or lipid source disclosed herein.

In some embodiments, the fat or lipid source provides from about 35% to about 55% of the total calories of the nutritional composition. In other embodiments, the fat or lipid source provides from about 40% to about 47% of the total calories of the nutritional composition.

In certain embodiments the nutritional composition may be formulated such that from about 10% to about 23% of the total calories of the nutritional composition are provided by sunflower oil. In other embodiments, from about 13% to about 20% of the total calories in the nutritional composition may be provided by sunflower oil. Still, in other embodiments, from about 15% to about 18% of the total calories of the nutritional composition may be provided by sunflower oil.

In some embodiments, the nutritional composition may be formulated such that from about 10% to about 20% of the total calories are provided by MCT oil. In certain embodiments, from about 12% to about 18% of the total calories in the nutritional composition may be provided by MCT oil.

Still, in certain embodiments, from about 14% to about 17% of the calories of the nutritional composition may be provided by MCT oil.

In some embodiments, the nutritional composition may be formulated such that from about 10% to 20% of the total calories of the nutritional composition are provided by soybean oil. In certain embodiments, from about 12% to about 18% of the total calories of the nutritional composition may be provided by soybean oil. In certain embodiments, from about 13% to about 16% of the total calories may be provided by soybean oil.

The nutritional composition of the present disclosure may comprise lactoferrin in some embodiments. Lactoferrins are single chain polypeptides of about 80 kD containing 1-4 glycans, depending on the species. The 3-D structures of lactoferrin of different species are very similar, but not identical. Each lactoferrin comprises two homologous lobes, called the N- and C-lobes, referring to the N-terminal and C-terminal part of the molecule, respectively. Each lobe further consists of two sub-lobes or domains, which form a cleft where the ferric ion ($Fe^{3+}$) is tightly bound in synergistic cooperation with a (bi)carbonate anion. These domains are called N1, N2, C1 and C2, respectively. The N-terminus of lactoferrin has strong cationic peptide regions that are responsible for a number of important binding characteristics. Lactoferrin has a very high isoelectric point (~pI 9) and its cationic nature plays a major role in its ability to defend against bacterial, viral, and fungal pathogens. There are several clusters of cationic amino acids residues within the N-terminal region of lactoferrin mediating the biological activities of lactoferrin against a wide range of microorganisms.

Lactoferrin for use in the present disclosure may be, for example, isolated from the milk of a non-human animal or produced by a genetically modified organism. The nutritional compositions described herein can, in some embodiments comprise non-human lactoferrin, non-human lactoferrin produced by a genetically modified organism and/or human lactoferrin produced by a genetically modified organism.

Suitable non-human lactoferrins for use in the present disclosure include, but are not limited to, those having at least 48% homology with the amino acid sequence of human lactoferrin. For instance, bovine lactoferrin ("bLF") has an amino acid composition which has about 70% sequence homology to that of human lactoferrin. In some embodiments, the non-human lactoferrin has at least 65% homology with human lactoferrin and in some embodiments, at least 75% homology. Non-human lactoferrins acceptable for use in the present disclosure include, without limitation, bLF, porcine lactoferrin, equine lactoferrin, buffalo lactoferrin, goat lactoferrin, murine lactoferrin and camel lactoferrin.

In some embodiments, the nutritional composition of the present disclosure comprises non-human lactoferrin, for example bovine lactoferrin (bLF). bLF is a glycoprotein that belongs to the iron transporter or transferrin family. It is isolated from bovine milk, wherein it is found as a component of whey. There are known differences between the amino acid sequence, glycosylation patters and iron-binding capacity in human lactoferrin and bLF. Additionally, there are multiple and sequential processing steps involved in the isolation of bLF from cow's milk that affect the physiochemical properties of the resulting bLF preparation. Human lactoferrin and bLF are also reported to have differences in their abilities to bind the lactoferrin receptor found in the human intestine.

Though not wishing to be bound by this or any other theory, it is believed that bLF isolated from whole milk has less lipopolysaccharide (LPS) initially bound than does bLF that has been isolated from milk powder. Additionally, it is believed that bLF with a low somatic cell count has less initially-bound LPS. A bLF with less initially-bound LPS has more binding sites available on its surface. This is thought to aid bLF in binding to the appropriate location and disrupting the infection process.

bLF suitable for the present disclosure may be produced by any method known in the art. For example, in U.S. Pat. No. 4,791,193, incorporated by reference herein in its entirety, Okonogi et al. discloses a process for producing bovine lactoferrin in high purity. Generally, the process as disclosed includes three steps. Raw milk material is first contacted with a weakly acidic cationic exchanger to absorb lactoferrin followed by the second step where washing takes place to remove nonabsorbed substances. A desorbing step follows where lactoferrin is removed to produce purified bovine lactoferrin. Other methods may include steps as described in U.S. Pat. Nos. 7,368,141, 5,849,885, 5,919,913 and 5,861,491, the disclosures of which are all incorporated by reference in their entirety.

In certain embodiments, lactoferrin utilized in the present disclosure may be provided by an expanded bed absorption ("EBA") process for isolating proteins from milk sources. In particular embodiments, the target protein is lactoferrin, though other milk proteins, such as lactoperoxidases or lactalbumins, also may be isolated. The expanded bed adsorption column can be any known in the art, such as those described in U.S. Pat. Nos. 7,812,138, 6,620,326, and 6,977,046, the disclosures of which are hereby incorporated by reference herein. EBA technology is further described in international published application nos. WO 92/00799, WO 02/18237, WO 97/17132, which are hereby incorporated by reference in their entireties.

In other embodiments, lactoferrin for use in the composition of the present disclosure can be isolated through the use of radial chromatography or charged membranes, as would be familiar to the skilled artisan.

The lactoferrin that is used in certain embodiments may be any lactoferrin isolated from whole milk and/or having a low somatic cell count, wherein "low somatic cell count" refers to a somatic cell count less than 200,000 cells/mL. By way of example, suitable lactoferrin is available from Tatua Co-operative Dairy Co. Ltd., in Morrinsville, New Zealand, from FrieslandCampina Domo in Amersfoort, Netherlands or from Fonterra Co-Operative Group Limited in Auckland, New Zealand. The nutritional composition may, in some embodiments, comprise lactoferrin in an amount from about 10 mg/100 mL to about 200 mg/100 mL. In other embodiments, lactoferrin is present in an amount from about 25 mg/100 mL to about 150 mg/100 mL. In other embodiments lactoferrin is present in an amount from about 60 mg/100 mL to about 120 mg/100 mL. In still other embodiments lactoferrin is present in an amount from about 85 mg/100 mL to about 110 mg/100 mL.

In certain embodiments lactoferrin is present in an amount of at least about 10 mg/100 kcal, at least about 15 mg/100 kcal, at least about 30 mg/100 kcal, at least about 50 mg/100 kcal, or at least about 100 mg/100 kcal. In certain embodiments, lactoferrin is present in an amount from about 10 mg/100 kcal to about 250 mg/100 kcal. In certain embodiments, lactoferrin is present in an amount from about 15 to about 300 mg lactoferrin per 100 kcal. In certain embodiments, lactoferrin is present in an amount from about 50 mg/100 kcal to about 175 mg/100 kcal. In certain embodiments, lactoferrin is present in an about from about 60 mg/100 kcal to about 150 mg per 100 kcal. In yet another embodiment, lactoferrin is present in an about from about 60 mg/100 kcal to about 100 mg/100 kcal. In still some embodiments, lactoferrin is present in an amount from about 100 mg/100 kcal to about 150 mg/100 kcals.

In an embodiment, the nutritional composition(s) of the present disclosure comprises choline. Choline is a nutrient that is essential for normal function of cells. It is a precursor for membrane phospholipids, and it accelerates the synthesis and release of acetylcholine, a neurotransmitter involved in memory storage. Moreover, though not wishing to be bound by this or any other theory, it is believed that dietary choline and docosahexaenoic acid (DHA) act synergistically to promote the biosynthesis of phosphatidylcholine and thus help promote synaptogenesis in human subjects. Additionally, choline and DHA may exhibit the synergistic effect of promoting dendritic spine formation, which is important in the maintenance of established synaptic connections. In some embodiments, the nutritional composition(s) of the present disclosure includes about 40 mg choline per serving to about 100 mg per 8 oz. serving.

In an embodiment, the nutritional composition comprises a source of iron. In an embodiment, the source of iron is ferric pyrophosphate, ferric orthophosphate, ferrous fumarate or a mixture thereof and the source of iron may be encapsulated in some embodiments.

One or more vitamins and/or minerals may also be added in to the nutritional composition in amounts sufficient to supply the daily nutritional requirements of a subject. It is to be understood by one of ordinary skill in the art that vitamin and mineral requirements will vary, for example, based on the age of the subject. For instance, an infant may have different vitamin and mineral requirements than a child between the ages of one and thirteen years. Thus, the embodiments are not intended to limit the nutritional composition to a particular age group but, rather, to provide a range of acceptable vitamin and mineral components.

In certain embodiments, the composition may optionally include, but is not limited to, one or more of the following vitamins or derivations thereof: vitamin B1 (thiamin, thiamin pyrophosphate, TPP, thiamin triphosphate, TTP, thiamin hydrochloride, thiamin mononitrate), vitamin B2 (riboflavin, flavin mononucleotide, FMN, flavin adenine dinucleotide, FAD, lactoflavin, ovoflavin), vitamin B3 (niacin, nicotinic acid, nicotinamide, niacinamide, nicotinamide adenine dinucleotide, NAD, nicotinic acid mononucleotide, NicMN, pyridine-3-carboxylic acid), vitamin B3-precursor tryptophan, vitamin B6 (pyridoxine, pyridoxal, pyridoxamine, pyridoxine hydrochloride), pantothenic acid (pantothenate, panthenol), folate (folic acid, folacin, pteroylglutamic acid), vitamin B12 (cobalamin, methylcobalamin, deoxyadenosylcobalamin, cyanocobalamin, hydroxycobalamin, adenosylcobalamin), biotin, vitamin C (ascorbic acid), vitamin A (retinol, retinyl acetate, retinyl palmitate, retinyl esters with other long-chain fatty acids, retinal, retinoic acid, retinol esters), vitamin D (calciferol, cholecalciferol, vitamin D3, 1,25-dihydroxyvitamin D), vitamin E (α-tocopherol, α-tocopherol acetate, α-tocopherol succinate, α-tocopherol nicotinate, α-tocopherol), vitamin K (vitamin K1, phylloquinone, naphthoquinone, vitamin K2, menaquinone-7, vitamin K3, menaquinone-4, menadione, menaquinone-8, menaquinone-8H, menaquinone-9, menaquinone-9H, menaquinone-10, menaquinone-11, menaquinone-12, menaquinone-13), choline, inositol, β-carotene and any combinations thereof.

In other embodiments, the composition may optionally include, but is not limited to, one or more of the following minerals or derivations thereof: boron, calcium, calcium acetate, calcium gluconate, calcium chloride, calcium lactate, calcium phosphate, calcium sulfate, chloride, chromium, chromium chloride, chromium picolonate, copper, copper sulfate, copper gluconate, cupric sulfate, fluoride, iron, carbonyl iron, ferric iron, ferrous fumarate, ferric orthophosphate, iron trituration, polysaccharide iron, iodide, iodine, magnesium, magnesium carbonate, magnesium hydroxide, magnesium oxide, magnesium stearate, magnesium sulfate, manganese, molybdenum, phosphorus, potassium, potassium phosphate, potassium iodide, potassium chloride, potassium acetate, selenium, sulfur, sodium, docusate sodium, sodium chloride, sodium selenate, sodium molybdate, zinc, zinc oxide, zinc sulfate and mixtures thereof. Non-limiting exemplary derivatives of mineral compounds include salts, alkaline salts, esters and chelates of any mineral compound.

The minerals can be added to growing-up milks or to other children's nutritional compositions in the form of salts such as calcium phosphate, calcium glycerol phosphate, sodium citrate, potassium chloride, potassium phosphate, magnesium phosphate, ferrous sulfate, zinc sulfate, cupric sulfate, manganese sulfate, and sodium selenite. Additional vitamins and minerals can be added as known within the art.

In an embodiment, the children's nutritional composition may contain between about 10 and about 50% of the maximum dietary recommendation for any given country, or between about 10 and about 50% of the average dietary recommendation for a group of countries, per serving of vitamins A, C, and E, zinc, iron, iodine, selenium, and choline. In another embodiment, the children's nutritional composition may supply about 10-30% of the maximum dietary recommendation for any given country, or about 10-30% of the average dietary recommendation for a group of countries, per serving of B-vitamins. In yet another embodiment, the levels of vitamin D, calcium, magnesium, phosphorus, and potassium in the children's nutritional product may correspond with the average levels found in milk. In other embodiments, other nutrients in the children's nutritional composition may be present at about 20% of the maximum dietary recommendation for any given country, or about 20% of the average dietary recommendation for a group of countries, per serving.

The children's nutritional composition of the present disclosure may optionally include one or more of the following flavoring agents, including, but not limited to, flavored extracts, volatile oils, cocoa or chocolate flavorings, peanut butter flavoring, cookie crumbs, vanilla or any commercially available flavoring. Examples of useful flavorings include, but are not limited to, pure anise extract, imitation banana extract, imitation cherry extract, chocolate extract, pure lemon extract, pure orange extract, pure peppermint extract, honey, imitation pineapple extract, imitation rum extract, imitation strawberry extract, or vanilla extract; or volatile oils, such as balm oil, bay oil, bergamot oil, cedarwood oil, cherry oil, cinnamon oil, clove oil, or peppermint oil; peanut butter, chocolate flavoring, vanilla cookie crumb, butterscotch, toffee, and mixtures thereof. The amounts of flavoring agent can vary greatly depending upon the flavoring agent used. The type and amount of flavoring agent can be selected as is known in the art.

The nutritional compositions of the present disclosure may optionally include one or more emulsifiers that may be added for stability of the final product. Examples of suitable emulsifiers include, but are not limited to, lecithin (e.g., from egg or soy), alpha lactalbumin and/or mono- and di-glycerides, and mixtures thereof. Other emulsifiers are readily apparent to the skilled artisan and selection of suitable emulsifier(s) will depend, in part, upon the formulation and final product.

The incorporation of certain ingredients (e.g., HMOs) described herein into a nutritional composition, such as an infant formula, may require the presence of at least one emulsifier to ensure that the ingredient does not separate from the fat or proteins contained within the infant formula during shelf-storage or preparation.

In some embodiments, the nutritional composition may be formulated to include from about 0.5 wt % to about 1 wt % of emulsifier based on the total dry weight of the nutritional composition. In other embodiments, the nutritional composition may be formulated to include from about 0.7 wt % to about 1 wt % of emulsifier based on the total dry weight of the nutritional composition.

In some embodiments where the nutritional composition is a ready-to-use liquid composition, the nutritional composition may be formulated to include from about 200 mg/L to about 600 mg/L of emulsifier. Still, in certain embodiments, the nutritional composition may include from about 300 mg/L to about 500 mg/L of emulsifier. In other embodiments, the nutritional composition may include from about 400 mg/L to about 500 mg/L of emulsifier.

The nutritional compositions of the present disclosure may optionally include one or more preservatives that may also be added to extend product shelf life. Suitable preservatives include, but are not limited to, potassium sorbate, sodium sorbate, potassium benzoate, sodium benzoate, potassium citrate, calcium disodium EDTA, and mixtures thereof. The incorporation of a preservative in the nutritional composition ensures that the nutritional composition has a suitable shelf-life such that, once reconstituted for administration, the nutritional composition delivers nutrients that are bioavailable and/or provide health and nutrition benefits for the target subject.

In some embodiments the nutritional composition may be formulated to include from about 0.1 wt % to about 1.0 wt % of a preservative based on the total dry weight of the composition. In other embodiments, the nutritional composition may be formulated to include from about 0.4 wt % to about 0.7 wt % of a preservative based on the total dry weight of the composition.

In some embodiments where the nutritional composition is a ready-to-use liquid composition, the nutritional composition may be formulated to include from about 0.5 g/L to about 5 g/L of preservative. Still, in certain embodiments, the nutritional composition may include from about 1 g/L to about 3 g/L of preservative.

The nutritional compositions of the present disclosure may optionally include one or more stabilizers. Suitable stabilizers for use in practicing the nutritional composition of the present disclosure include, but are not limited to, gum arabic, gum ghatti, gum karaya, gum tragacanth, agar, furcellaran, guar gum, gellan gum, locust bean gum, pectin, low methoxyl pectin, gelatin, microcrystalline cellulose, CMC (sodium carboxymethylcellulose), methylcellulose hydroxypropyl methyl cellulose, hydroxypropyl cellulose, DATEM (diacetyl tartaric acid esters of mono- and diglycerides), dextran, carrageenan, and mixtures thereof.

Incorporating a suitable stabilizer in the nutritional composition ensures that the nutritional composition has a suitable shelf-life such that, once reconstituted for administration, the nutritional composition delivers nutrients that are bioavailable and/or provide health and nutrition benefits for the target subject.

In some embodiments where the nutritional composition is a ready-to-use liquid composition, the nutritional composition may be formulated to include from about 50 mg/L to about 150 mg/L of stabilizer. Still, in certain embodiments, the nutritional composition may include from about 80 mg/L to about 120 mg/L of stabilizer.

The nutritional compositions of the disclosure may provide minimal, partial or total nutritional support. The compositions may be nutritional supplements or meal replacements. The compositions may, but need not, be nutritionally complete. In an embodiment, the nutritional composition of the disclosure is nutritionally complete and contains suitable types and amounts of lipid, carbohydrate, protein, vitamins and minerals. The amount of lipid or fat typically can vary from about 2 to about 7 g/100 kcal. The amount of protein typically can vary from about 1 to about 5 g/100 kcal. The amount of carbohydrate typically can vary from about 8 to about 14 g/100 kcal.

In some embodiments, the nutritional composition of the present disclosure is a growing-up milk. Growing-up milks are fortified milk-based beverages intended for children over 1 year of age (typically from 1-6 years of age). They are not medical foods and are not intended as a meal replacement or a supplement to address a particular nutritional deficiency. Instead, growing-up milks are designed with the intent to serve as a complement to a diverse diet to provide additional insurance that a child achieves continual, daily intake of all essential vitamins and minerals, macronutrients plus additional functional dietary components, such as non-essential nutrients that have purported health-promoting properties.

The exact composition of an infant formula or a growing-up milk or other nutritional composition according to the present disclosure can vary from market-to-market, depending on local regulations and dietary intake information of the population of interest. In some embodiments, nutritional compositions according to the disclosure consist of a milk protein source, such as whole or skim milk, plus added sugar and sweeteners to achieve desired sensory properties, and added vitamins and minerals. The fat composition is typically derived from the milk raw materials. Total protein can be targeted to match that of human milk, cow milk or a lower value. Total carbohydrate is usually targeted to provide as little added sugar, such as sucrose or fructose, as possible to achieve an acceptable taste. Typically, Vitamin A, calcium and Vitamin D are added at levels to match the nutrient contribution of regional cow milk. Otherwise, in some embodiments, vitamins and minerals can be added at levels that provide approximately 20% of the dietary reference intake (DRI) or 20% of the Daily Value (DV) per serving. Moreover, nutrient values can vary between markets depending on the identified nutritional needs of the intended population, raw material contributions and regional regulations.

The pediatric subject may be a child or an infant. For example, the subject may an infant ranging in age from 0 to 3 months, about 0 to 6 months, 0 to 12 months, 3 to 6 months, or 6 to 12 months. The subject may alternatively be a child ranging in age from 1 to 13 years, 1 to 6 years or 1 to 3 years. In an embodiment, the composition may be administered to the pediatric subject prenatally, during infancy, and during childhood.

EXAMPLE

Example 1

This example illustrates a method for producing a partially hydrolyzed casein which is enriched with beta-casein protein. Beta-casein enriched casein protein is dispersed in water with temperature about 55° C. The pH of the slurry is adjusted with sodium and/or potassium hydroxide to the range from about 6 to 9, preferably 7.0. The enzyme of trypsin and chymotrypsin, or trypsin-like and chymotrypsin-like enzymes from animal and/or microbial sources are added into the slurry. The incubation time may be from 2 to 6 hours. At the end of digestion, the slurry is heat treated to inactivate the enzymes (e.g., 10 minutes at temperature of 85-90° C.). The hydrolysate slurry obtained from the process could be further centrifuged or filtered to clarify and remove large particles and protein aggregates, or large protein/peptides molecules if ultrafiltration and/or nanofiltration is used. The hydrolysate could be also dried to get a powdered product.

Example 2

Table 1 provides an exemplary nutritional formulation comprising an exemplary beta-casein enriched casein hydrolysate as described herein.

TABLE 1

| Nutrient | Unit | Per 100 kcal |
|---|---|---|
| Cow's milk protein | g | 1.89 |
| Beta-casein enriched casein hydrolysate | g | 0.21 |
| Fat | g | 5.3 |
| Linoleic Acid | mg | 810 |
| Alpha-Linolenic Acid | mg | 71 |
| Docosahexaenoic Acid | mg | 17.8 |
| Arachidonic Acid | mg | 36 |
| Carbohydrates | g | 11.2 |
| GOS | g | 0.31 |
| Polydextrose | g | 0.31 |
| Vitamin A | µg | 84 |
| Vitamin D | µg | 1.55 |
| Vitamin E | mg | 1.27 |
| Vitamin K | µg | 7.2 |
| Thiamin | µg | 85 |
| Riboflavin | µg | 170 |
| Vitamin B6 | µg | 60 |
| Vitamin B12 | µg | 0.31 |
| Niacin | µg | 660 |
| Folic Acid | µg | 18 |
| Pantothenic Acid | µg | 570 |
| Biotin | µg | 2.7 |
| Vitamin C | mg | 18 |
| Sodium | mg | 28 |
| Potassium | mg | 110 |
| Chloride | mg | 65 |
| Calcium | mg | 79 |
| Phosphorus | mg | 48 |
| Magnesium | mg | 8 |
| Iodine | µg | 17 |
| Iron | mg | 1 |
| Copper | µg | 65 |
| Zinc | mg | 0.8 |
| Manganese | µg | 18 |
| Selenium | µg | 2.7 |

TABLE 1-continued

| Nutrient | Unit | Per 100 kcal |
|---|---|---|
| Choline | mg | 24 |
| Inositol | mg | 8.5 |
| Carnitine | mg | 2 |
| Taurine | mg | 6 |
| Total Nucleotides | mg | 3.1 |
| Lactoferrin | g | 0.09 |

Although preferred embodiments of the disclosure have been described using specific terms, devices, and methods, such description is for illustrative purposes only. The words used are words of description rather than of limitation. It is to be understood that changes and variations may be made by those of ordinary skill in the art without departing from the spirit or the scope of the present disclosure, which is set forth in the following claims. In addition, it should be understood that aspects of the various embodiments may be interchanged in whole or in part. Therefore, the spirit and scope of the appended claims should not be limited to the description of the preferred versions contained therein.

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references.

What is claimed is:

1. A nutritional composition comprising:
   a milk protein preparation, the milk protein preparation comprising: a casein, acid casein or caseinate,
   wherein the milk protein preparation is hydrolyzed with at least two proteases selected from the group consisting of: trypsin; proteolytic enzymes that cleave peptide bonds following a positively charged amino acid; chymotrypsin; proteolytic enzymes that cleave peptide bonds following a tyrosine, phenylalanine or tryptophan residue; pepsin; and plasmin to form a protein hydrolysate,
   wherein the protein hydrolysate comprises alpha-casein peptides, beta-casein peptides, and kappa-casein peptides,
   wherein the beta-casein peptides in the protein hydrolysate comprise about 25% to about 60% of the total peptides in the nutritional composition, and
   wherein the kappa-casein peptides in the protein hydrolysate comprise about 1% to about 10% of the total peptides in the nutritional composition.

2. The nutritional composition of claim 1, wherein the beta-casein peptides in the protein hydrolysate comprise about 30% to about 50% of the total peptides in the nutritional composition.

3. The nutritional composition of claim 1, wherein the beta-casein peptides in the protein hydrolysate comprise about 35% to about 45% of the total peptides in the nutritional composition.

4. The nutritional composition of claim 1, wherein the alpha-casein peptides in the protein hydrolysate comprise about 5% to about 25% of the total peptides in the nutritional composition.

5. The nutritional composition of claim 1, wherein the casein, acid casein or caseinate is hydrolyzed using one or more of trypsin; proteolytic enzymes that cleave peptide bonds following a positively charged amino acid; chymotrypsin; proteolytic enzymes that cleave peptide bonds following a tyrosine, phenylalanine or tryptophan residue; pepsin; and plasmin.

6. The nutritional composition of claim 1, wherein the casein, acid casein or caseinate is beta-casein enriched and the beta-casein enriched casein, acid casein or caseinate comprises between about 40% to about 95% beta-casein.

7. The nutritional composition of claim 1, wherein the casein, acid casein or caseinate is alpha-casein enriched and the alpha-casein enriched casein, acid casein or caseinate comprises between about 50% to about 95% alpha-casein.

8. The nutritional composition of claim 1, wherein the casein, acid casein or caseinate is kappa-casein enriched and the kappa-enriched casein, acid casein or caseinate comprises between about 15% to about 95% kappa-casein.

9. The nutritional composition of claim 1 further comprising at least one hydrolysate of polymeric immunoglobulin receptor (PIGR), osteopontin, bile-salt activated lipase and/or clusterin.

10. The nutritional composition of claim 1 further comprising one or more of:
    a protein source;
    a lipid source;
    a carbohydrate source;
    a prebiotic;
    a probiotic;
    at least one human milk oligosaccharide (HMO);
    a long chain polyunsaturated fatty acid; and/or
    a source of β-glucan.

11. A nutritional composition comprising:
    a protein hydrolysate, the protein hydrolysate comprising alpha-casein peptides, beta-casein peptides, and kappa-casein peptides,
    wherein the beta-casein peptides in the protein hydrolysate comprise about 25% to about 60% of the total peptides in the nutritional composition, and
    wherein the kappa-casein peptides in the protein hydrolysate comprise about 1% to about 10% of the total peptides in the nutritional composition.

12. The nutritional composition of claim 11, wherein the beta-casein peptides in the protein hydrolysate comprise about 30% to about 50% of the total peptides in the nutritional composition.

13. The nutritional composition of claim 11, wherein the beta-casein peptides in the protein hydrolysate comprise about 35% to about 45% of the total peptides in the nutritional composition.

14. The nutritional composition of claim 11, wherein the alpha-casein peptides in the protein hydrolysate comprise about 5% to about 25% of the total peptides in the nutritional composition.

15. The nutritional composition of claim 11, wherein the casein, acid casein or caseinate is hydrolyzed using one or more of trypsin; proteolytic enzymes that cleave peptide bonds following a positively charged amino acid; chymotrypsin; proteolytic enzymes that cleave peptide bonds following a tyrosine, phenylalanine or tryptophan residue; pepsin; and plasmin.

16. The nutritional composition of claim 11, wherein the casein, acid casein or caseinate is beta-casein enriched and the beta-casein enriched casein, acid casein or caseinate comprises between about 40% to about 95% beta-casein.

17. The nutritional composition of claim 11, wherein the casein, acid casein or caseinate is alpha-casein enriched and the alpha-casein enriched casein, acid casein or caseinate comprises between about 50% to about 95% alpha-casein.

18. The nutritional composition of claim 11, wherein the casein, acid casein or caseinate is kappa-casein enriched and the kappa-enriched casein, acid casein or caseinate comprises between about 15% to about 95% kappa-casein.

19. The nutritional composition of claim 11 further comprising at least one hydrolysate of polymeric immunoglobulin receptor (PIGR), osteopontin, bile-salt activated lipase and/or clusterin.

20. The nutritional composition of claim 11 further comprising one or more of:
    a protein source;
    a lipid source;
    a carbohydrate source;
    a prebiotic;
    a probiotic;
    at least one human milk oligosaccharide (HMO);
    a long chain polyunsaturated fatty acid; and/or
    a source of β-glucan.

* * * * *